US012290663B2

(12) United States Patent
Fabricius et al.

(10) Patent No.: US 12,290,663 B2
(45) Date of Patent: *May 6, 2025

(54) FRONT LOADED AUTO INJECTOR FOR ADMINISTERING A MEDICAMENT

(71) Applicant: Ascendis Pharma A/S, Hellerup (DK)

(72) Inventors: Paul Erik Fabricius, Holstebro (DK); Jan Olesen, Holstebro (DK); Steen Jensen, Dragør (DK); Henrik Egesborg, Hellerup (DK); Per Mølgaard Pedersen, Struer (DK)

(73) Assignee: Ascendis Pharma A/S, Hellerup (DK)

( * ) Notice: Subject to any disclaimer, the term of this patent is extended or adjusted under 35 U.S.C. 154(b) by 78 days.

This patent is subject to a terminal disclaimer.

(21) Appl. No.: 18/112,265

(22) Filed: Feb. 21, 2023

(65) Prior Publication Data
US 2023/0270945 A1 Aug. 31, 2023

Related U.S. Application Data

(63) Continuation of application No. 16/060,630, filed as application No. PCT/EP2016/082858 on Dec. 29, 2016, now Pat. No. 11,607,496.

(30) Foreign Application Priority Data

Dec. 30, 2015 (EP) .................................... 15203168
Sep. 23, 2016 (EP) .................................... 16190461

(51) Int. Cl.
*A61M 5/20* (2006.01)
*A61M 5/24* (2006.01)
(Continued)

(52) U.S. Cl.
CPC ............ *A61M 5/2066* (2013.01); *A61M 5/20* (2013.01); *A61M 5/24* (2013.01);
(Continued)

(58) Field of Classification Search
CPC ........ A61M 5/2066; A61M 5/20; A61M 5/24; A61M 5/31511; A61M 5/31573;
(Continued)

(56) References Cited

U.S. PATENT DOCUMENTS

| 4,024,864 A | 5/1977 | Davies |
| 4,394,863 A | 7/1983 | Bartner |

(Continued)

FOREIGN PATENT DOCUMENTS

| CN | 101905048 | 12/2010 |
| CN | 102413855 | 4/2012 |

(Continued)

OTHER PUBLICATIONS

US 11,957,880 B2, 04/2024, Jensen et al. (withdrawn)
(Continued)

*Primary Examiner* — Lauren P Farrar
(74) *Attorney, Agent, or Firm* — Knobbe, Martens, Olson & Bear, LLP

(57) ABSTRACT

Disclosed is a method for controlling an auto injector and an auto injector for administering a medicament from a cartridge having a first cartridge end and a second cartridge end and having a cartridge outlet at the first cartridge end, the cartridge comprising a cartridge compartment with a first cartridge subcompartment containing a first medicament component of the medicament and a second cartridge subcompartment containing a second medicament component of the medicament. The auto injector comprises: a housing; a cartridge receiver; a cartridge sensor; a drive module; an orientation sensor; and a processing unit.

35 Claims, 13 Drawing Sheets

(51) Int. Cl.
*A61M 5/315* (2006.01)
*A61M 5/32* (2006.01)

(52) U.S. Cl.
CPC .... *A61M 5/31511* (2013.01); *A61M 5/31573* (2013.01); *A61M 5/31576* (2013.01); *A61M 5/326* (2013.01); *A61M 2005/2411* (2013.01); *A61M 2005/31588* (2013.01); *A61M 2005/3267* (2013.01); *A61M 2205/332* (2013.01); *A61M 2205/3368* (2013.01); *A61M 2205/50* (2013.01); *A61M 2205/502* (2013.01); *A61M 2205/6063* (2013.01); *A61M 2205/82* (2013.01); *A61M 2205/8206* (2013.01)

(58) Field of Classification Search
CPC .............. A61M 5/31576; A61M 5/326; A61M 2005/2411; A61M 2005/31588; A61M 2005/3267; A61M 2205/332; A61M 2205/3368; A61M 2205/50; A61M 2205/502; A61M 2205/6063; A61M 2205/82; A61M 2205/8206
See application file for complete search history.

(56) References Cited

U.S. PATENT DOCUMENTS

| | | | |
|---|---|---|---|
| 4,677,980 A | 7/1987 | Reilly et al. | |
| 5,739,508 A | 4/1998 | Uber, III | |
| 5,808,203 A | 9/1998 | Nolan, Jr. et al. | |
| 6,368,314 B1 | 4/2002 | Kipfer et al. | |
| 9,173,995 B1 | 11/2015 | Tucker | |
| 10,384,031 B1* | 8/2019 | Acker | A61M 16/20 |
| 10,835,677 B2 | 11/2020 | Fabricius et al. | |
| 11,179,524 B2 | 11/2021 | Pedersen et al. | |
| 11,351,305 B2 | 6/2022 | Pedersen et al. | |
| 11,406,760 B2 | 8/2022 | Olesen et al. | |
| 11,517,673 B2 | 12/2022 | Pedersen et al. | |
| 11,524,115 B2 | 12/2022 | Jacobsen et al. | |
| 11,607,496 B2 | 3/2023 | Fabricius et al. | |
| 11,738,147 B2 | 8/2023 | Olesen et al. | |
| 11,969,581 B2 | 4/2024 | Pedersen et al. | |
| 12,005,241 B2 | 6/2024 | Pedersen et al. | |
| 2002/0016573 A1 | 2/2002 | Munk | |
| 2002/0107477 A1 | 8/2002 | Kipfer | |
| 2003/0083626 A1 | 5/2003 | Munk et al. | |
| 2003/0205587 A1 | 11/2003 | Tribe | |
| 2005/0261634 A1 | 11/2005 | Karlsson | |
| 2006/0178630 A1 | 8/2006 | Bostrom et al. | |
| 2009/0036846 A1 | 2/2009 | Dacquay et al. | |
| 2009/0209883 A1* | 8/2009 | Higgins | A61B 5/15169 345/169 |
| 2009/0299328 A1 | 12/2009 | Mudd et al. | |
| 2010/0069842 A1 | 3/2010 | Dos Santos et al. | |
| 2010/0094309 A1 | 4/2010 | Boukhny et al. | |
| 2010/0211005 A1 | 8/2010 | Edwards et al. | |
| 2011/0313395 A1 | 12/2011 | Krulevitch et al. | |
| 2012/0078185 A1 | 3/2012 | Smith et al. | |
| 2012/0204997 A1 | 8/2012 | Winn et al. | |
| 2012/0283655 A1 | 11/2012 | Plumptre et al. | |
| 2013/0079708 A1 | 3/2013 | Wiimpenny et al. | |
| 2013/0193073 A1 | 8/2013 | Hogard et al. | |
| 2013/0211326 A1 | 8/2013 | Dasbach et al. | |
| 2013/0211327 A1 | 8/2013 | Osman et al. | |
| 2013/0226134 A1 | 8/2013 | Schabbach et al. | |
| 2013/0245545 A1 | 9/2013 | Arnold et al. | |
| 2013/0281965 A1* | 10/2013 | Kamen | G16H 20/17 604/67 |
| 2013/0296807 A1* | 11/2013 | Lintern | A61M 5/158 604/404 |
| 2014/0012229 A1 | 1/2014 | Bokelman et al. | |
| 2014/0114277 A1* | 4/2014 | Eggert | A61M 5/34 604/500 |
| 2014/0142514 A1 | 5/2014 | Elahi et al. | |
| 2014/0166915 A1 | 6/2014 | Ishibashi et al. | |
| 2014/0188076 A1 | 7/2014 | Kamen et al. | |
| 2014/0193788 A1 | 7/2014 | Groves et al. | |
| 2014/0207106 A1* | 7/2014 | Bechmann | A61M 5/2033 604/506 |
| 2014/0221925 A1* | 8/2014 | Kondoh | A61M 5/31568 604/111 |
| 2014/0358093 A1 | 12/2014 | Soerensen et al. | |
| 2015/0045729 A1* | 2/2015 | Denzer | A61J 1/065 604/110 |
| 2015/0051538 A1 | 2/2015 | Hata et al. | |
| 2015/0088089 A1* | 3/2015 | Bartlett, II | A61M 5/2448 604/403 |
| 2015/0122338 A1 | 5/2015 | Hunter et al. | |
| 2015/0231334 A1 | 8/2015 | Buchine et al. | |
| 2015/0306316 A1 | 10/2015 | Bruggemann | |
| 2015/0320932 A1 | 11/2015 | Draper et al. | |
| 2015/0359967 A1 | 12/2015 | Steel et al. | |
| 2015/0367074 A1 | 12/2015 | Draper et al. | |
| 2015/0367075 A1 | 12/2015 | Cave | |
| 2015/0374930 A1 | 12/2015 | Hyde et al. | |
| 2017/0119969 A1 | 5/2017 | McCullough et al. | |
| 2017/0196702 A1 | 7/2017 | Agarwal | |
| 2018/0094309 A1 | 4/2018 | Boukhany | |
| 2018/0236181 A1 | 8/2018 | Marlin et al. | |
| 2020/0384207 A1 | 12/2020 | Egesborg et al. | |
| 2022/0152310 A1 | 5/2022 | Pedersen et al. | |
| 2022/0288316 A1 | 9/2022 | Olesen et al. | |
| 2023/0016657 A1 | 1/2023 | Pedersen et al. | |
| 2023/0072178 A1 | 3/2023 | Jacobsen et al. | |
| 2023/0090661 A1 | 3/2023 | Jensen et al. | |
| 2023/0263961 A1 | 8/2023 | Egesborg et al. | |
| 2023/0338659 A1 | 10/2023 | Olesen et al. | |
| 2024/0082494 A1 | 3/2024 | Jensen et al. | |
| 2024/0165336 A1 | 5/2024 | Pedersen et al. | |
| 2024/0277944 A1 | 8/2024 | Pedersen et al. | |
| 2024/0374827 A1 | 11/2024 | Egesborg et al. | |

FOREIGN PATENT DOCUMENTS

| | | |
|---|---|---|
| CN | 102740907 | 10/2012 |
| CN | 103813820 | 5/2014 |
| CN | 105492047 | 4/2016 |
| EP | 2656865 | 10/2013 |
| EP | 2675500 | 12/2013 |
| EP | 2777731 | 9/2014 |
| EP | 2923715 | 9/2015 |
| GB | 2356349 | 5/2001 |
| GB | 2506918 | 4/2014 |
| JP | H11513586 | 11/1999 |
| JP | 2000-513973 | 10/2000 |
| JP | 2001-513371 | 9/2001 |
| JP | 2005-503202 | 2/2005 |
| JP | 2005-080832 | 3/2005 |
| JP | 2007-500531 | 1/2007 |
| JP | 2008-531235 | 8/2008 |
| JP | 2009-148591 | 7/2009 |
| JP | 2009-279438 | 12/2009 |
| JP | 2010-506681 | 3/2010 |
| JP | 2010-510011 | 4/2010 |
| JP | 2010-523181 | 7/2010 |
| JP | 2011-507668 | 3/2011 |
| JP | 2011-521744 | 7/2011 |
| JP | 2011-240159 | 12/2011 |
| JP | 2012-505066 | 3/2012 |
| JP | 2012-066767 | 4/2012 |
| JP | 2012-516737 | 7/2012 |
| JP | 2012-519028 A | 8/2012 |
| JP | 2013-506444 | 2/2013 |
| JP | 2013-069305 | 4/2013 |
| JP | 2013-075154 | 4/2013 |
| JP | 2013-537844 | 10/2013 |
| JP | 2014-500746 | 1/2014 |
| JP | 2014-502890 | 2/2014 |
| JP | 2014-503279 | 2/2014 |
| JP | 2014-506159 | 3/2014 |
| JP | 2014-507223 | 3/2014 |
| JP | 2014-515941 | 7/2014 |
| JP | 2014-516700 | 7/2014 |

(56) References Cited

FOREIGN PATENT DOCUMENTS

| | | |
|---|---|---|
| JP | 2014-516702 | 7/2014 |
| JP | 2014-521113 | 8/2014 |
| JP | 2014-528787 | 10/2014 |
| JP | 2014-4528787 | 10/2014 |
| JP | 2015-521920 | 8/2015 |
| JP | 2015-163208 | 9/2015 |
| JP | 2016-208611 | 12/2016 |
| KR | 10-2015-0125701 | 11/2015 |
| KR | B-10-1666755 | 10/2016 |
| KR | 10-2017-0013870 | 2/2017 |
| PT | 3397321 | 10/2022 |
| RU | 2014-120469 | 11/2015 |
| WO | WO 2002/051471 | 7/2002 |
| WO | WO 2005/102416 | 11/2005 |
| WO | WO 2006/116997 | 11/2006 |
| WO | WO 2008/062025 | 5/2008 |
| WO | WO 2006/059597 | 6/2008 |
| WO | WO 2010/098927 | 9/2010 |
| WO | WO 2010/098931 | 9/2010 |
| WO | WO 2012/112347 | 8/2012 |
| WO | WO 2010/100883 | 9/2012 |
| WO | WO 2012/160157 | 11/2012 |
| WO | WO 2013/065055 | 5/2013 |
| WO | WO 2013/138830 | 9/2013 |
| WO | WO 2014/008393 | 1/2014 |
| WO | WO 2012/066767 | 5/2014 |
| WO | WO 2014/118106 | 8/2014 |
| WO | WO 2014/118109 | 8/2014 |
| WO | WO 2014/118110 | 8/2014 |
| WO | WO 2014/144096 | 9/2014 |
| WO | WO 2014/166915 | 10/2014 |
| WO | WO 2014/168205 | 10/2014 |
| WO | WO 2014/187812 | 11/2014 |
| WO | WO 2014/187813 | 11/2014 |
| WO | WO 2015/006430 | 1/2015 |
| WO | WO 2013/069305 | 4/2015 |
| WO | WO 2015/055640 | 4/2015 |
| WO | WO 2015/055642 | 4/2015 |
| WO | WO 2015/115326 | 8/2015 |
| WO | WO 2015/187797 | 12/2015 |
| WO | WO 2016/005421 | 1/2016 |
| WO | WO 2016/033507 | 3/2016 |
| WO | WO 2016/098060 | 6/2016 |
| WO | WO 2014/091765 | 1/2017 |
| WO | WO 2017/009724 | 1/2017 |
| WO | WO 2017/114906 | 7/2017 |
| WO | WO 2017/114907 | 7/2017 |
| WO | WO 2017/114908 | 7/2017 |
| WO | WO 2017/114909 | 7/2017 |
| WO | WO 2017/114910 | 7/2017 |
| WO | WO 2017/114911 | 7/2017 |
| WO | WO 2017/114912 | 7/2017 |
| WO | WO 2018/215516 | 11/2018 |
| WO | WO 2019/002534 | 1/2019 |
| WO | WO 2020/176319 | 9/2020 |
| WO | WO 2023/052487 | 4/2023 |

OTHER PUBLICATIONS

Office Action in New Zealand Application No. 742526, dated Jul. 6, 2023, in 10 pages.
Office Action in Canadian Application No. 3,064,056, dated Jul. 11, 2023, in 5 pages.
English translation of Office Action issued in Japanese Application No. JP 2023-021789, dated Nov. 7, 2023, in 5 pages.
Office Action with English translation in Korean application No. 10-2023-7043623, dated Apr. 18, 2024, in 12 pages.
Office Action with English translation in Japanese Application No. JP 2023-140873, mailed on Jun. 28, 2024, in 11 pages.
Hearing Notice dispatched on Dec. 29, 2023 in India Patent Application No. 201947041763.
English Translation of Office Action dated Jun. 3, 2021, in Corresponding Chinese Application No. 201880043795.0.
English Translation of Office Action dated Jul. 9, 2021, in corresponding Russian Application No. 2019140269.
English Translation of Office Action dated Jul. 30, 2021, in corresponding Russian Application No. 2020103216.
English Translation of Office Action dated Jun. 10, 2021, in corresponding Chinese Application No. 201880033657.4.
English translation of Office Action issued in Japanese Application No. 2019-565323, dated Jan. 5, 2022.
English translation of Office Action issued in Japanese Application No. 2019-570894, dated Jan. 13, 2022.
English translation of Office Action issued in Chinese Application No. 201880033657, dated Feb. 23, 2022.
English translation of Office Action issued in Japanese Application No. 2021-116315, dated Sep. 2, 2022.
English translation of Office Action issued in Korean Application No. 10-2020-7000564, dated Oct. 17, 2022.
European Search Report for EP 15203132.4, dated Jun. 29, 2016.
European Search Report for EP 15203137.3, dated Jul. 1, 2016.
Partial European Search Report for EP15203168.8, dated Sep. 16, 2016.
European Search Report for EP 18733296.0, dated Feb. 1, 2023, in 5 pages.
International Search Report for PCT/EP2016/082861, dated Mar. 22, 2017.
International Preliminary Report on Patentability for PCT/EP2016/082861, mailed Jul. 12, 2018.
International Search Report for PCT/EP2016/082856, mailed on Mar. 28, 2017.
International Preliminary Report on Patentability for PCT/EP2016/082856, mailed Jul. 12, 2018.
International Search Report for PCT/EP2016/082860, mailed on May 3, 2017.
International Preliminary Report on Patentability for PCT/EP2016/082860, mailed on Jul. 12, 2018.
International Search Report for PCT/EP2016/082858, mailed Mar. 24, 2017.
International Preliminary Report on Patentability for PCT/EP2016/082858, mailed on Jul. 12, 2018.
International Search Report for PCT/EP2016/082855, mailed Mar. 24, 2017.
International Preliminary Report on Patentability for PCT/EP2016/082855, mailed on Jul. 12, 2018.
International Search Report for PCT/EP2016/082857, mailed May 12, 2017.
International Preliminary Report on Patentability for PCT/EP2016/082857, mailed on Jul. 12, 2018.
International Search Report for PCT/EP2016/082859, mailed on Apr. 10, 2017.
International Preliminary Report on Patentability for PCT/EP2016/082859, mailed on Jul. 12, 2018.
International Search Report for PCT/EP2018/063460, mailed on Mar. 7, 2018.
International Preliminary Report on Patentability for PCT/EP2018/063460, mailed on Dec. 5, 2019.
International Search Report for PCT/EP2018/067532, mailed on Sep. 25, 2018.
International Preliminary Report on Patentability for PCT/EP2018/067532, mailed on Jan. 9, 2020.
Office Action in Canadian Application No. 3,006,626, dated Dec. 19, 2022, in 5 pages.
Office Action in Canadian Application No. 3,006,616, dated Dec. 19, 2022, in 3 pages.
Office Action in Canadian Application No. 3,006,638, dated Jan. 17, 2023, in 4 pages.
Office Action in Canadian Application No. 3,006,627, dated Dec. 30, 2022, in 5 pages.
Office Action in Canadian Application No. 3,006,643, dated Jan. 4, 2023, in 7 pages.
Office Action in Canadian Application No. 3,006,622, dated Jan. 4, 2023, in 4 pages.
Office Action in New Zealand Application No. 742523, dated Feb. 27, 2023, in 3 pages.

(56) References Cited

OTHER PUBLICATIONS

Office Action in New Zealand Application No. 742538, dated Mar. 8, 2023, in 9 pages.
Office Action in New Zealand Application No. 742526, dated Mar. 13, 2023, in 8 pages.
Office Action in Australian Application No. 2018-294519, dated Mar. 10, 2023, in 3 pages.
English translation of Office Action issued in Japanese Application No. JP 2022-074131, dated Apr. 21, 2023, in 2 pages.
English translation of Office Action issued in Japanese Application No. JP 2021-116315, dated Apr. 25, 2023, in 3 pages.
Office Action with English translation in Japanese application No. 2023-140873, mailed on Jan. 29, 2025, in 4 pages.
European Search Report in application No. EP 24203896.6, dated Jan. 7, 2025, in 10 pages.
Office Action with English translation issued in Japanese application No. 2024-014677, mailed on Sep. 12, 2024, in 5 pages.
English translation of Office Action received in Japanese application No. 2023-218327, dated Oct. 18, 2024, in 5 pages.

\* cited by examiner

FRONT LOADED AUTO INJECTOR FOR ADMINISTERING A MEDICAMENT

CROSS REFERENCE TO RELATED APPLICATIONS

This application is a continuation of U.S. application Ser. No. 16/060,630, filed Jun. 8, 2018, which is a U.S. National Phase Application of PCT International Application Number PCT/EP2016/082858, filed on Dec. 29, 2016, designating the United States of America and published in the English language, which is an International Application of and claims the benefit of priority to European Patent Application No. 15203168.8, filed on Dec. 30, 2015 and European Patent Application No. 16190461.0, filed on Sep. 23, 2016. The disclosures of the above-referenced applications are hereby expressly incorporated by reference in their entireties.

FIELD

The present disclosure relates to an auto injector, such as an electronic auto injector, a cartridge for an auto injector, a system comprising an auto injector and a cartridge, and a method for operating an auto injector.

INTRODUCTION/BACKGROUND

Hypodermic syringes are widely used to deliver fluids to the body. It is known to have hypodermic syringes applicable for manual operation. However, auto injectors, such as electronic auto injectors, have been developed and are widely used to aid the administering of fluid or medicaments to the body.

To avoid relying on users correctly performing certain tasks, it is of increasing interest that the auto injector automatically carries out as much as possible of the injection process. Especially, when administering of the medicament requires several steps, such as if medicament needs to be mixed prior to injection, it may be beneficial to automate the process of preparing and administering the fluid, such as a medicament.

SUMMARY

There is a need for an auto injector, such as an electronic auto injector, with an improved automation of preparing and administering the medicament. The present disclosure provides an auto injector, a cartridge, a system, and a method improving the preparation and administering of medicament with an auto injector.

Accordingly, an auto injector for preparing and/or administering a medicament from a cartridge is disclosed. The cartridge has a first cartridge end and a second cartridge end and having a cartridge outlet at the first cartridge end. The cartridge comprises a cartridge compartment. The cartridge compartment has a first cartridge subcompartment containing a first medicament component of the medicament and a second cartridge subcompartment containing a second medicament component of the medicament.

The auto injector comprising: a housing; a cartridge receiver; a cartridge sensor; a drive module; an orientation sensor; and a processing unit.

The cartridge receiver has a cartridge receiver opening. The cartridge receiver is configured to receive the cartridge by insertion of the second end of the cartridge through the cartridge receiver opening.

The cartridge sensor is configured to detect reception of the cartridge in the cartridge receiver and provide a cartridge detection signal indicative of the cartridge being received in the cartridge receiver.

The drive module is coupled to move a plunger rod between a retracted plunger rod position and an extended plunger rod position. The plunger rod is configured to move the first stopper, e.g. when the plunger rod is moved towards the extended plunger rod position.

The orientation sensor is configured to provide an orientation signal indicative of the orientation of the cartridge, e.g. when the cartridge is received in the cartridge receiver.

The processing unit is coupled to the orientation sensor, the cartridge sensor, and to the drive module.

The processing unit is configured to: receive a first input signal; receive the cartridge detection signal; receive the orientation signal; control the drive module to move the plunger rod to a mix plunger rod position following reception of the cartridge detection signal and the first input signal; and control the drive module to move the plunger rod to a prime plunger rod position following completion of movement of the plunger rod to the mix plunger rod position.

The processing unit may further be configured to receive a trigger event; and control the drive module to move the plunger rod to an injection plunger rod position following reception of the trigger event after completion of movement of the plunger rod to the prime plunger rod position.

Also disclosed is a cartridge for an auto injector, such as the disclosed auto injector. The cartridge has a first cartridge end and a second cartridge end and having a cartridge outlet at the first cartridge end. The cartridge comprises a cartridge compartment. The cartridge compartment has a first cartridge subcompartment containing a first medicament component of the medicament and a second cartridge subcompartment containing a second medicament component of the medicament. The cartridge is configured to be received by a cartridge receiver of an auto injector, such as a cartridge receiver of the disclosed auto injector, by insertion of the second end of the cartridge through the cartridge receiver opening of the auto injector.

Also disclosed is a system comprising an auto injector, such as the disclosed auto injector, and a cartridge, such as the disclosed cartridge.

Also disclosed is a method for operating an auto injector, such as the disclosed auto injector, e.g. an auto injector comprising a plunger rod and a cartridge receiver configured to receive a cartridge, such as the disclosed cartridge, e.g. a cartridge having a first cartridge end and a second cartridge end and having a cartridge outlet at the first cartridge end.

The method comprises: receiving a first input signal; detecting reception of the cartridge in the cartridge receiver; determining orientation of the cartridge; moving the plunger rod to a mix plunger rod position following detection of the cartridge being received in the cartridge receiver and reception of the first input signal; and moving the plunger rod to a prime plunger rod position following completion of movement of the plunger rod to the mix plunger rod position.

The method may further comprise receiving a trigger event; and moving the plunger rod to an injection plunger rod position following reception of the trigger event after completion of movement of the plunger rod to the prime plunger rod position.

The trigger event may, for example, be an effect of a push of a button, an effect of an elapsed timeout, and/or an effect of a predetermined user behaviour. The trigger event may be indicative of the auto injector being pressed against the injection site.

It is an advantage of the present disclosure that the steps involved in preparing and/or administering a medicament are increasingly automated. It is further an advantage that such increased automation provides for increased safety in preparing and/or administering the medicament.

It is a further advantage of the present disclosure that an auto injector may be provided which is easier to use, and reduce the risk of erroneous administering of a medicament.

It is an advantage of the present disclosure that it may aid in determining characteristics of the received cartridge. It is a further advantage of the disclosure that an auto injector may be operated according to characteristics of the received cartridge.

The disclosure may enable determination or indication that the cartridge received is a used cartridge and/or a flawed cartridge and/or a counterfeit cartridge and/or a cartridge comprising a medicament not approved for the device. Thus, an advantage of the disclosure may be that it increases the safety of an auto injector, e.g. as the auto injector may be prevented or restricted from using a not new cartridge.

Thus, it is a further advantage of the present disclosure, that patient safety is increased, e.g. by decreasing the risk of transmitting infections, and/or by decreasing the risk of incorrect dosage of medicament.

It is envisaged that any embodiments or elements as described in connection with any one aspect may be used with any other aspects or embodiments, mutatis mutandis.

The cartridge has a cartridge outlet at the first cartridge end. The cartridge may comprise a cartridge back face, e.g. at the second cartridge end, such as opposite the cartridge outlet. The cartridge back face may comprise a cartridge back end opening. The cartridge back end opening may provide access for a plunger rod, such as the plunger rod of the auto injector, to the first stopper.

The cartridge compartment may contain the medicament. The cartridge outlet may be configured for fluid communication with the compartment, e.g. at the first cartridge end. The cartridge may be configured to expel medicament through the cartridge outlet. The cartridge outlet may be configured to be coupled with a needle, such as a hypodermic needle, to provide the medicament to be expelled through the needle.

The cartridge comprises a first stopper movable inside the cartridge compartment. The cartridge may comprise a second stopper movable inside the cartridge compartment. The second stopper may be between the first stopper and the cartridge outlet. The cartridge may comprise a third stopper movable inside the cartridge compartment. The third stopper may be between the second stopper and the cartridge outlet. The first stopper, the second stopper, and/or the third stopper may be movable inside the cartridge compartment towards the cartridge outlet, e.g. in a first stopper direction, such as towards the first cartridge end. For example, the medicament may be expelled through the cartridge outlet upon movement of the first stopper, the second stopper, and/or the third stopper, e.g. in the first stopper direction and/or towards the cartridge outlet.

The cartridge may be a dual-chamber cartridge. The cartridge compartment may have a first cartridge subcompartment and a second cartridge subcompartment. The first cartridge subcompartment may be between the first stopper and the second stopper. The second cartridge subcompartment may be between the second stopper and the cartridge outlet and/or the third stopper.

The first cartridge subcompartment may contain a first medicament component of the medicament. The second cartridge subcompartment may contain a second medicament component of the medicament. Each of the first medicament component and/or second medicament component may be a powder composition, a fluid, a liquid, a gel, a gas, and/or any combination thereof. The first medicament component and/or the second medicament component may be solute, such as a powder composition. The first medicament component and/or the second medicament component may be a solvent, such as a fluid composition, such as a liquid composition. The second medicament component may be a powder composition and the first medicament component may be a fluid composition, e.g. water or ethanol or saline solution or buffer solution or preservative solution. The second medicament component may be a solute. The first medicament component may be a solvent. It is envisaged that the medicament may be any medicament being injectable via a hypodermic needle, for example after reconstitution of the medicament. The medicament may be a growth hormone. The medicament may be human growth hormone. The medicament may be a depot version, such as a long-acting version, of human growth hormone. The second medicament component may be a powder composition of human growth hormone.

The cartridge may have a bypass section providing fluid communication between the first cartridge subcompartment and the second cartridge subcompartment, e.g. when the second stopper is positioned in the bypass section. The cartridge may have a plurality of bypass sections providing fluid communication between neighbouring cartridge subcompartments, e.g. when a stopper separating the neighbouring cartridge subcompartment is positioned in the bypass section.

A reusable auto injector, such as the disclosed auto injector, may be especially useful when the cartridge comprises a plurality of subcompartments. For example an auto injector for a multi compartment or multi chamber cartridge may be more advanced, and therefore it may be beneficial to allow the auto injector to be used more than one time. For example, the auto injector may provide automated processes for mixing medicament components, such as for mixing medicament components initially provided in different subcompartments of the cartridge.

The cartridge may be comprised as part of a cartridge assembly. The cartridge assembly may comprise the cartridge. Additionally, the cartridge assembly may comprise a needle, such as a needle assembly comprising a needle, a needle cover, a cartridge holder, and/or a cartridge code feature.

The cartridge assembly may comprise the needle, such as the needle assembly comprising the needle. The needle assembly may comprise a needle cover and/or a needle hub. The cartridge assembly may comprise a cartridge holder. The cartridge holder may be configured to engage with the needle assembly. The cartridge holder may provide for attachment of the needle assembly to the cartridge.

The cartridge may comprise a cartridge code feature and/or the cartridge assembly may comprise the cartridge and the cartridge code feature. The cartridge code feature may comprise one or more of a colour, a bar code, an RFID tag, an NFC tag, an identification number, and a QR code. For example, the cartridge code feature may comprise a colour and/or a sequence of colours. The cartridge code feature may be positioned surrounding or partly surrounding a part of the cartridge compartment wherein a stopper, such as the first stopper, is initially positioned. Such position of the cartridge code feature may increase readability of the cartridge code feature, e.g. since the stopper may form a background for the cartridge code feature. The stopper, such as the first stopper may be a light colour, such as light grey or white. The stopper, such as the first stopper, may be a dark colour, such as dark blue, dark grey, or black. The stopper may form a dark background for the cartridge code feature. The stopper, such as the first stopper, may reduce reflection of light, e.g. to further increase readability of the cartridge code feature.

The cartridge code feature may be positioned at a specific position on the cartridge, e.g. independently of the stopper(s), such as the first stopper. For example, the cartridge code feature may be positioned at a code distance from the second cartridge end. All cartridges may have their cartridge code features positioned at the same position, e.g. positioned at the code distance from the second cartridge end. Such uniform position of the cartridge code feature may decrease complexity, and decrease size, of the auto injector, as the cartridge code feature is read in the same position for all suitable cartridges.

The cartridge and the cartridge code feature may be manufactured as one element. For example, the cartridge code feature may be a certain form of the cartridge. Alternatively, the cartridge code feature may be attached to the cartridge, such as fastened, e.g. by glue, to the cartridge. For example, the cartridge code feature may be a colour code printed on the cartridge.

The cartridge code feature may be indicative of one or more cartridge specifications, such as medicament in the cartridge, concentration of medicament in the cartridge, viscosity of medicament in the cartridge, volume and/or mass of medicament in the cartridge, positions of stopper(s) in the cartridge compartment, etc. The cartridge code feature may be indicative of a position of the first stopper wherein air in the cartridge compartment is reduced, such as minimized and/or reduced to an amount appropriate for injection. The cartridge code feature may be indicative of the amount of medicament contained in the cartridge. The cartridge code feature may be indicative of a specific type of cartridge, such as an ID number of the specific type of cartridge. The auto injector, such as the processing unit of the auto injector, may be configured to determine one or more cartridge specifications based on an ID number, e.g. by table lookup. The cartridge code feature may be indicative of a suitable, such as optimal, speed of stopper movement, such as stopper movement in different phases of movement, such as during mixing, during air-shot, and/or injection. The cartridge code feature may be indicative of a suitable, such as optimal, speed of movement of the first stopper, such as speed of movement of the first stopper in different phases of movement, such as during mixing, during air-shot, and/or injection. The cartridge code feature may be indicative of time needed for optimal mixing of the first medicament component and the second medicament component.

The cartridge code feature may be indicative of a suitable dwell time for the medicament, e.g. time to ensure that the medicament is distributed into the tissue, e.g. favourable time to wait after injection before retraction of the needle.

The auto injector may be a front-loaded auto injector. The auto injector comprises a cartridge receiver configured to receive the cartridge. The cartridge receiver may be configured to receive a cartridge assembly comprising the cartridge. The cartridge assembly may comprise a cartridge holder. The cartridge receiver has a cartridge receiver opening. The cartridge receiver may be configured to receive the cartridge by insertion of the cartridge, such as the second end of the cartridge, through the cartridge receiver opening. The cartridge may be inserted in a cartridge receiving direction. The cartridge receiving direction may be opposite the first stopper direction, e.g. when the cartridge is received in the cartridge receiver. The cartridge may be in a first angular position when inserted into the cartridge receiver. The cartridge may be retained in the cartridge receiver in a second angular position, e.g. after insertion of the cartridge in the cartridge receiver.

The cartridge receiver may be configured to receive a cartridge assembly comprising the cartridge and a cartridge holder. The cartridge assembly may be retained in the cartridge receiver by one or more cartridge retention members of the cartridge holder engaging with members of the cartridge receiver.

The cartridge and/or cartridge assembly may be lockable in the cartridge receiver, e.g. the cartridge and/or cartridge assembly may be locked in the cartridge receiver to prevent removal of the cartridge and/or cartridge assembly from the cartridge receiver. The cartridge and/or cartridge assembly may be locked in the cartridge receiver by movement of a plunger rod of the auto injector.

The auto injector may comprise a cartridge sensor. The cartridge receiver may comprise the cartridge sensor. The cartridge sensor may be configured to detect reception of the cartridge and/or cartridge assembly in the cartridge receiver. The cartridge sensor may provide a cartridge sensor signal indicative of whether the cartridge and/or cartridge assembly is received in the cartridge receiver. The cartridge sensor may provide a cartridge detection signal indicative of the cartridge and/or cartridge assembly being received in the cartridge receiver. The cartridge sensor signal may comprise the cartridge detection signal.

The auto injector may be an electronic auto injector. The auto injector may comprise a battery. The housing may accommodate the battery. The battery may be a rechargeable battery. For example, the battery may be a Li-ion battery or a NiCd battery or a NiMH battery. The battery may be configured to be charged by connection of a charger.

The auto injector comprises a drive module. The drive module may be coupled to move, such as actuate, such as advance, a plunger rod, such as between a retracted plunger rod position and an extended plunger rod position. Movement of the plunger rod may provide the cartridge and/or cartridge assembly to be locked in the cartridge receiver. For example, the cartridge and/or cartridge assembly may be locked in the cartridge receiver by advancement of the plunger rod from a retracted plunger rod position.

The drive module may comprise one or more electrical elements. The drive module may be configured to receive electrical power from the battery. The drive module may be electrically connected to the battery for receiving electrical power. The drive module may be accommodated by the housing. The drive module may comprise a motor, such as an electro-mechanical motor, such as a DC motor, e.g. a DC motor with or without brushes. The drive module may comprise a solenoid motor. The drive module may comprise a shape memory metal engine. The drive module may comprise an arrangement of springs configured to actuate the plunger rod. The drive module may comprise a pressurized gas configured to actuate the plunger rod.

The auto injector may comprise a plunger rod, such as the plunger rod movable by the drive module. The plunger rod may be configured to move a stopper, such as the first stopper of the cartridge. For example, when the plunger rod is moved towards the extended plunger rod position the plunger rod may be configured to move the first stopper towards the cartridge outlet, such as to expel medicament from the cartridge compartment through the cartridge outlet and/or to expel air from the cartridge compartment through the cartridge outlet.

The plunger rod may be moved to a pre-mix plunger rod position, such as towards the extended plunger rod position, such as from the retracted plunger rod position. The pre-mix plunger rod position may be a position wherein fluid communication between the first cartridge subcompartment and the second cartridge subcompartment is not yet established.

The plunger rod may be moved to a mix plunger rod position, such as towards the extended plunger rod position, such as from the retracted plunger rod position and/or the pre-mix plunger rod position. The mix plunger rod position may be a position wherein the first medicament component and the second medicament component are mixed, such as combined. The mix plunger rod position may be a position wherein the second stopper is positioned in the bypass section, such as to provide fluid communication between the first cartridge subcompartment and the second cartridge subcompartment.

The plunger rod may be moved to a prime plunger rod position, such as towards the extended plunger rod position, such as from the retracted plunger rod position and/or the mix plunger rod position. The prime plunger rod position may be a position wherein air has been expelled from the cartridge compartment. For example, the prime plunger rod position may be selected to position the first stopper in a position wherein air in the cartridge compartment is reduced, such as minimized and/or reduced to an amount appropriate for injection.

The plunger rod may be moved to an injection plunger rod position, such as towards the extended plunger rod position, such as from the retracted plunger rod position and/or the prime plunger rod position. The injection plunger rod position may be a position wherein the medicament has been expelled and/or injected from the cartridge compartment. For example, the injection plunger rod position may be selected to position the first stopper in a position wherein medicament in the cartridge compartment is reduced, such as minimized, such as in a position close to the cartridge outlet. The injection plunger rod position may be the extended plunger rod position.

The plunger rod may be moved towards the retracted plunger rod position, e.g. to the retracted plunger rod position. For example, the plunger rod may be moved towards the retracted plunger rod position, e.g. to the retracted plunger rod position, after completion of injection, such as from the injection plunger rod position and/or the extended plunger rod position.

The processing unit may be configured to move the plunger rod to the pre-mix plunger rod position, the mix plunger rod position, the prime plunger rod position, the injection plunger rod position, the extended plunger rod position and/or the retracted plunger rod position.

The auto injector may comprise an ejection sensor, such as a plunger rod position sensor. The ejection sensor may be configured to detect the ejection, such as the expelling, of medicament and/or air in the cartridge compartment. The ejection sensor may be configured to detect and/or determine the position of the plunger rod and/or the position of the first stopper. The ejection sensor may be configured to detect conditions indicative of the position of the plunger rod and/or the position of the first stopper. The ejection sensor may be configured to provide an ejection sensor signal. The ejection sensor signal may be indicative of the position of the plunger rod and/or the first stopper.

The ejection sensor may comprise a tachometer, e.g. a tachometer of the drive module. The tachometer may be configured to count the revolutions of the drive module, such as a motor of the drive module, such as the revolutions of the drive module from a set point, such as a point wherein the position of the plunger rod is known, such as the retracted plunger rod position of the plunger rod. The count of revolutions of the drive module may be used to determine the actual position of the plunger rod, such as the pre-mix plunger rod position, the mix plunger rod position, the prime plunger rod position, the injection plunger rod position, the extended plunger rod position and/or the retracted plunger rod position.

The processing unit may be coupled to the ejection sensor, such as to the tachometer. The processing unit may receive from the ejection sensor a first ejection sensor signal, such as a tachometer signal, indicative of the count of revolutions of the drive module. The processing unit may determine the position of the plunger rod based on the first ejection sensor signal. The processing unit may receive a second ejection sensor signal, e.g. from the ejection sensor, indicative of the plunger rod being in a known position, such as the retracted plunger rod position. The processing unit may determine the position of the plunger rod based on the first ejection sensor signal and the second ejection sensor signal.

The cartridge may be lockable in the cartridge receiver, e.g. the cartridge may be locked in the cartridge receiver to prevent removal of the cartridge from the cartridge receiver. Movement of the plunger rod towards the extended plunger rod position may lock the cartridge in the cartridge receiver. For example, movement of the plunger rod to the mix plunger rod position may lock the cartridge in the cartridge receiver. Movement of the plunger rod towards the retracted plunger rod position may unlock the cartridge from the cartridge receiver. For example, movement of the plunger rod to the retracted plunger rod position may unlock the cartridge in the cartridge receiver. The cartridge may be locked in the cartridge receiver when the plunger rod is not in the retracted plunger rod position and/or close to the retracted plunger rod position. Coupling the position of the plunger rod with the locking of the cartridge in the cartridge receiver may provide the advantage that the release of the cartridge may be restricted or prevented when the auto injector is active.

The auto injector may comprise an orientation sensor. The orientation sensor may be configured to provide an orientation signal indicative of the orientation of the cartridge, e.g. when the cartridge is received in the cartridge receiver. The orientation signal may be indicative of the orientation of the cartridge relative to gravity, such as relative to the direction of gravity.

The orientation sensor may be configured to detect an orientation of the cartridge and/or an orientation indicative of the orientation of the cartridge, such as an orientation of the auto injector. The detected orientation may be relative to gravity, such as relative to the direction of gravity. The orientation sensor may be configured to detect the direction of gravity, and/or if the direction of gravity is within a certain range of a predetermined direction. The orientation sensor may comprise an accelerometer. The orientation sensor may comprise a plurality of accelerometers, such as three accelerometers, such as three accelerometers arranged to detect acceleration in three dimensions, such as a three-dimensional accelerometer. The orientation sensor may comprise a tilt sensor, a tri-axial accelerometer, a single axis accelerometer, a magnetometer and/or any combination thereof, and the orientation sensor may provide a measure of roll, pitch and azimuth, a measure of acceleration and/or tilt in one or more directions.

The orientation sensor may be configured to detect if the cartridge is in a predetermined orientation. The orientation sensor may be configured to detect if the orientation of the auto injector is indicative of the cartridge being in the predetermined orientation. The predetermined orientation may be a vertical orientation. The predetermined orientation may be an orientation within 45 degrees of vertical, such as within 30 degrees of vertical. The predetermined orientation may be an orientation wherein the cartridge is orientated such that a longitudinal axis of the cartridge is within 45 degrees of vertical, such as within 30 degrees of vertical, and wherein the cartridge outlet is above the cartridge compartment, such as in a vertical position above the cartridge compartment.

The processing unit may be coupled to the orientation sensor. The processing unit may be configured to receive the orientation signal, e.g. indicative of the orientation of the cartridge when received in the cartridge receiver, and/or of the auto injector.

Movement of the plunger rod to the mix plunger rod position and/or to the prime plunger rod position and/or to the injection plunger rod position may be based on the orientation of the cartridge, e.g. on the orientation signal. For example, movement of the plunger rod to the mix plunger rod position and/or to the prime plunger rod position and/or to the injection plunger rod position may require that a tilt angle between vertical and a longitudinal axis extending along the cartridge is within 45 degrees, such as within 30 degrees, and/or that the cartridge outlet is in a vertical position above the cartridge compartment.

Control of the drive module to move the plunger rod to the mix plunger rod position and/or to the prime plunger rod position and/or to the injection plunger rod position may be based on the orientation of the cartridge, e.g. on the orientation signal.

The processing unit may be configured to control the drive module based on the orientation signal. For example, the processing unit may be configured to control the drive module to move the plunger rod to the mix plunger rod position and/or to the prime plunger rod position and/or to the injection plunger rod position based on the orientation signal. For example, the processing unit may be configured to control the drive module to move the plunger rod to the mix plunger rod position and/or to the prime plunger rod position and/or to the injection plunger rod position only if the orientation signal indicates that a tilt angle between vertical and a longitudinal axis extending along the cartridge is within 45 degrees, such as within 30 degrees, of vertical, and/or if the cartridge outlet is in a vertical position above the cartridge compartment.

The auto injector may comprise a code sensor. The code sensor may be configured to read a cartridge code feature, such as the cartridge code feature of the cartridge e.g. indicative of one or more cartridge specifications. The code sensor may be configured to provide a code signal indicative of the cartridge code feature. The processing unit may be coupled to the code sensor. The processing unit may be configured to receive the code signal.

The processing unit may be configured to determine an unauthorized cartridge, such as a counterfeit cartridge and/or a used cartridge, and/or a tampered cartridge, and/or a cartridge containing a wrong dose, and/or a cartridge containing a wrong medicament, based on the code signal.

The code sensor may comprise an optical sensor. The code sensor may comprise an optical sensor comprising a transmitter and a receiver, such as a light transmitter and a light receiver. The code sensor may be configured to read the cartridge code feature. The code sensor may be configured to read colour codes, bar codes, RFID tags, NFC tags, identification numbers, QR codes, and/or any combination hereof.

Movement of the plunger rod may be based on the code signal. For example, movement of the plunger rod to the mix plunger rod position and/or the prime plunger rod position and/or the injection plunger rod position, may be based on the cartridge code feature, e.g. on the code signal. For example, control of the drive module to move the plunger rod to the prime plunger rod position may be based on the code signal. The processing unit may be configured to control the drive module based on the code signal. For example, the processing unit may be configured to control the drive module to move the plunger rod to the prime plunger rod position based on the code signal.

Basing the movement of the plunger rod on cartridge specification, e.g. on the code signal, provides that the plunger rod movement may be optimized to several types of cartridges. For example, the air-shot may be performed with reduced or no expelling of medicament, thereby increasing dosage accuracy and/or reducing patient discomfort, e.g. even with different cartridges.

Basing the movement of the plunger rod on cartridge specification, e.g. on the code signal, provides that the plunger rod movement may be optimized to several types of cartridges. For example, the plunger rod may be kept in a mix plunger rod position for a time depending on the cartridge specification following detection of the cartridge being received in the cartridge receiver and reception of the first input signal thereby ensuring appropriate mixing and/or reducing patient discomfort, e.g. even with different cartridges.

The auto injector may comprise a resistance sensor. The resistance sensor may be configured to provide a resistance signal. The resistance signal may be indicative of resistance against movement of the plunger rod. The processing unit may be coupled to the resistance sensor. The processing unit may be configured to receive the resistance signal.

The processing unit may be configured to determine an unauthorized cartridge, such as a counterfeit cartridge and/or a used cartridge, and/or a tampered cartridge, and/or a cartridge containing a wrong dose, and/or a cartridge containing a wrong medicament, based on the code signal and/or the resistance signal.

The resistance signal may be indicative of resistance against movement of the plunger rod in one direction, such as movement towards the extended plunger rod position. For example, the resistance signal may be indicative of the force necessary to move the plunger rod, e.g. towards the extended plunger rod position.

The resistance sensor may be configured to determine electrical power consumed by the drive module, e.g. by measuring electrical resistance, electrical current, and/or electrical voltage of the drive module and/or a combination thereof. The resistance sensor may comprise an electrical resistance sensor, an electrical current sensor, and/or an electrical voltage sensor. The drive module may comprise the resistance sensor.

The resistance sensor may be configured to measure pressure and/or force applied to a plunger rod front end of the plunger rod. The plunger rod front end may be configured to engage with the first stopper of the cartridge. The resistance sensor may be configured to measure pressure and/or force between the plunger rod and the stopper. For example, the resistance sensor may comprise a pressure transducer and/or a force transducer on the plunger rod front end. The plunger rod may comprise the resistance sensor.

Movement of the plunger rod may be based on the resistance signal. For example, movement of the plunger rod to the mix plunger rod position and/or the prime plunger rod position and/or the injection plunger rod position, may be based on resistance against movement of the plunger rod, e.g. on the resistance signal. For example, control of the drive module to move the plunger rod to the mix plunger rod position may be based on the resistance signal. The processing unit may be configured to control the drive module based on the resistance signal. For example, the processing unit may be configured to control the drive module to move the plunger rod to the mix plunger rod position based on the resistance signal.

Movement of the plunger rod to the mix plunger rod position and/or the prime plunger rod position and/or the injection plunger rod position may require that resistance against movement of the plunger rod is above a low resistance threshold, e.g. that the resistance signal indicates resistance against movement of the plunger rod above a low resistance threshold. For example, the processing unit may be configured to control the drive module to move the plunger rod to the mix plunger rod position only if the resistance signal indicates resistance against movement of the plunger rod above a low resistance threshold, such as after completion of movement of the plunger rod to the pre-mix plunger rod position. The low resistance threshold may be between 1 N and 15 N, such as between 5 N and 11 N. The low resistance threshold may be 1 N, 5 N, or 10 N.

A cartridge parameter may be based on resistance against movement of the plunger rod, e.g. on the resistance signal. The processing unit may be configured to determine the cartridge parameter based on the resistance signal.

The cartridge parameter may be indicative of the cartridge being unused and/or full. For example, if the present plunger rod position has reached a plunger rod threshold, such as a predetermined plunger rod position between the retracted plunger rod position and the extended plunger rod position, and the resistance signal is indicative of resistance against movement of the plunger rod above the low resistance threshold, e.g. indicating a sufficient force necessary to move the plunger rod, hence indicating that the plunger rod has engaged the first stopper.

The cartridge parameter may be indicative of the cartridge being not full and/or empty, such as used. For example, if the present plunger rod position has reached a plunger rod threshold, such as a predetermined plunger rod position between the retracted plunger rod position and the extended plunger rod position, and the resistance signal is indicative of resistance against movement of the plunger rod below the low resistance threshold, e.g. indicating a small force necessary to move the plunger rod, hence indicating that the first stopper is in an advanced position.

The cartridge parameter may be indicative of the cartridge being flawed and/or that no needle is attached and/or attached needle is blocked, e.g. if the resistance signal is indicative of resistance against movement of the plunger rod above a high resistance threshold, e.g. indicating a large force necessary to move the plunger rod, hence indicating that the plunger rod and/or the first stopper is somehow blocked from advancement. The high resistance threshold may be between 8 N and 25 N, such as between 10 N and 20 N. The high resistance threshold may be 8 N, 11 N, or 15 N.

Thresholds, such as the plunger rod threshold, the low resistance threshold and/or the high resistance threshold, may be determined based on the cartridge and/or the cartridge code feature. The cartridge code feature may be indicative of the threshold, such as the plunger rod threshold, the low resistance threshold and/or the high resistance threshold.

The processing unit may be configured to determine the threshold, such as the plunger rod threshold, the low resistance threshold and/or the high resistance threshold, based on the code signal.

The auto injector may comprise a temperature sensor. The temperature sensor may be configured to provide a temperature signal, such as a temperature signal indicative of the temperature of the auto injector and/or of the cartridge and/or of the medicament. The temperature sensor may comprise an infrared sensor, such as an infrared optical sensor.

The processing unit may be coupled to the temperature sensor. The processing unit may be configured to receive the temperature signal.

Movement of the plunger rod to the mix plunger rod position and/or to the prime plunger rod position and/or to the injection plunger rod position may be based on the temperature of the auto injector and/or of the cartridge and/or of the medicament, e.g. on the temperature signal.

The auto injector, such as the processing unit, may be configured to control the drive module based on the temperature signal. For example, the processing unit may be configured to control the drive module to move the plunger rod to the mix plunger rod position and/or to the prime plunger rod position and/or to the injection plunger rod position based on the temperature signal.

The auto injector may comprise an input device, such as a first input device. The first input device may be a button or a touch sensitive area or a microphone. The first input device may be configured to provide the first input signal. The first input signal may be indicative of a first user interaction with the first input device. The first input device may be configured to provide a second input signal. The second input signal may be indicative of a second user interaction with the first input device.

The processing unit may be coupled to the first input device. The processing unit may be configured to receive the first input signal and/or the second input signal. The processing unit may be configured to control the drive module to move the plunger rod to the mix plunger rod position only after receiving the first input signal. The processing unit may be configured to control the drive module to move the plunger rod to the prime plunger rod position only after receiving the second input signal.

The auto injector may comprise a contact member. The contact member may be configured to be pressed against the injection site. The contact member may be movable between an extended contact member position and a retracted contact member position. The contact member may be biased towards the extended contact member position, e.g. by a contact member spring. The contact member may be configured to be moved towards the retracted contact member position, e.g. when pressed against the injection site. The contact member and/or a contact member sensor may be configured to provide a contact member signal indicative of position of the contact member. The auto injector and/or the contact member may comprise a contact member sensor configured to detect the position of the contact member. The contact member sensor may be configured to provide the contact member signal indicative of the contact member.

The contact member may be in a first contact member position, e.g. between the extended contact member position and the retracted contact member position. The contact member being in the first contact member position may indicate that the contact member is close to the retracted contact member position. The contact member being in the first contact member position may indicate that the contact member is pressed against the injection site. The contact member being in the first contact member position may indicate that a needle positioned on the cartridge is pressed sufficiently into the skin for injection of the medicament to start.

The contact member may be in a second contact member position, e.g. between the extended contact member position and the retracted contact member position, such as between the extended contact member position and the first contact member position. The contact member being in the second contact member position may indicate that the contact member is restricted from being biased to the extended contact member position. The contact member being in the second contact member position may indicate that a needle cover, such as a needle with a needle cover, is positioned on the cartridge.

The processing unit may be coupled to the contact member. The processing unit may be configured to receive the contact member signal. The trigger event may comprise the contact member signal being indicative of the contact member being in a first contact member position. The contact member may be a trigger member.

The auto injector may comprise a needle sensor. The needle sensor may be configured to detect a needle, and/or a needle assembly, and/or a needle cover of a needle assembly, of the cartridge assembly, e.g. when the cartridge assembly is received in the auto injector and/or in the cartridge receiver of the auto injector. The needle sensor may provide a needle signal indicative of the presence of a needle, and/or a needle assembly, and/or a needle cover of a needle assembly.

The processing unit may be coupled to the needle sensor. The processing unit may be configured to receive the needle signal. The processing unit may be configured to control the drive module based on the needle signal. For example, the processing unit may be configured to control the drive module to start movement of the plunger rod only if a needle is present, and/or only if a needle cover is not present.

The needle sensor may comprise the contact member. For example, the contact member may be configured to be in the second contact member position if a needle cover, such as a needle with a needle cover, is present on the cartridge. Movement of the plunger rod may be based on the position of the contact member, e.g. on the contact member signal. Movement of the plunger rod to the mix plunger rod position and/or the prime plunger rod position and/or to the injection plunger rod position may be based on the position of the contact member, e.g. on the contact member signal. For example, the movement of the plunger rod to the mix plunger rod position and/or the prime plunger rod position and/or to the injection plunger rod position may require that the contact member signal is indicative of the contact member not being in the second contact member position, such as the contact member signal being indicative of the contact member being in the extended contact member position.

Alternatively or additionally, movement of the plunger rod to the mix plunger rod position and/or the prime plunger rod position and/or to the injection plunger rod position may be based on detection of a needle cover. For example, the movement of the plunger rod to the mix plunger rod position and/or the prime plunger rod position and/or to the injection plunger rod position may require that a needle cover is detected after reception of the cartridge in the cartridge receiver, and that afterwards no needle cover is detected, e.g. detection that the needle cover has been removed.

The processing unit may be configured to control the drive module to move the plunger rod to the mix plunger rod position and/or the prime plunger rod position and/or to the injection plunger rod based on the contact member signal. For example, the processing unit may be configured to control the drive module to move the plunger rod to the mix plunger rod position and/or the prime plunger rod position and/or to the injection plunger rod only if the contact member signal is indicative of the contact member not being in the second contact member position, such as the contact member signal being indicative of the contact member being in the extended contact member position.

Movement of the plunger rod may comprise movement having a plunger rod speed, such as a first plunger rod speed and/or a second plunger rod speed. The plunger rod speed may be based on the position of the plunger rod. The plunger rod may be moved to the pre-mix plunger rod position, such as from the retracted plunger rod position, with a pre-mix plunger rod speed. The plunger rod may be moved to the mix plunger rod position, such as from the pre-mix plunger rod position, with a mix plunger rod speed. The plunger rod may be moved to the prime plunger rod position, such as from the mix plunger rod position, with a prime plunger rod speed. The plunger rod may be moved to the injection plunger rod position, such as from the prime plunger rod position, with an injection plunger rod speed. The pre-mix plunger rod speed may be faster than the mix plunger rod speed. The mix-plunger rod speed may be between 1 mm/second and 3 mm/second, such as 1.7 mm/second.

The pre-mix plunger rod speed, the mix plunger rod speed, the prime plunger rod speed, and/or the injection plunger rod speed, may be based on a cartridge specification, such as on the cartridge code feature, such as on the code signal. The processing unit may be configured to determine the pre-mix plunger rod speed, the mix plunger rod speed, the prime plunger rod speed, and/or the injection plunger rod speed, based on the code signal.

The pre-mix plunger rod speed, the mix plunger rod speed, the prime plunger rod speed, and/or the injection plunger rod speed, may be based on temperature, such as temperature of the auto injector and/or of the cartridge and/or of the medicament, such as on the temperature signal. The processing unit may be configured to determine the pre-mix plunger rod speed, the mix plunger rod speed, the prime plunger rod speed, and/or the injection plunger rod speed, based on the temperature signal.

The processing unit may be configured to control the drive module to move the plunger rod to the pre-mix plunger rod position, such as from the retracted plunger rod position, with the pre-mix plunger rod speed. The processing unit may be configured to control the drive module to move the plunger rod to the mix plunger rod position, such as from the pre-mix plunger rod position, with the mix plunger rod speed. The processing unit may be configured to control the drive module to move the plunger rod to the prime plunger rod position, such as from the mix plunger rod position, with the prime plunger rod speed. The processing unit may be configured to control the drive module to move the plunger rod to the injection plunger rod position, such as from the prime plunger rod position, with the injection plunger rod speed.

The processing unit may be configured to control the drive module to move the plunger rod to the pre-mix plunger rod position following reception of the cartridge detection signal and the first input signal. The processing unit may be configured to control the drive module to move the plunger rod to the mix-plunger rod position following completion of movement of the plunger rod to the pre-mix plunger rod position.

Movements of the plunger rod, such as movement to the pre-mix plunger rod position, to the mix plunger rod position, to the prime plunger rod position, to the injection plunger rod position, and/or to the retracted plunger rod position, may be preceded by one or more elapsed time, such as delays. For example, movement of the plunger rod to the prime plunger rod position and/or movement of the plunger rod to the injection plunger rod position may require that a reconstitution time has elapsed since completion of the movement of the plunger rod to the mix plunger rod position. The reconstitution time may be chosen to allow sufficient time to ensure that the medicament is reconstituted, e.g. that the first medicament component and second medicament component has been sufficiently mixed. The reconstitution time may be based on a cartridge specification, e.g. the reconstitution time may be based on the cartridge code feature, e.g. the reconstitution time may be based on the code signal.

The processing unit may be configured to control the drive module to move the plunger rod to the mix plunger rod position and/or the prime plunger rod position and/or to the injection plunger rod position and/or the retracted plunger rod position based on the one or more elapsed time. For example, the processing unit may be configured to control the drive module to move the plunger rod to the prime plunger rod position only after the reconstitution time has elapsed since completion of the movement of the plunger rod to the mix plunger rod position. Alternatively or additionally, the processing unit may be configured to control the drive module to move the plunger rod to the injection plunger rod position only after the reconstitution time has elapsed since completion of the movement of the plunger rod to the mix plunger rod position.

The plunger rod may be moved towards the retracted plunger rod position, such as to the retracted plunger rod position, following completion of the movement of the plunger rod to the injection plunger rod position. The processing unit may be configured to control the drive module to move the plunger rod towards the retracted plunger rod position following completion of the movement of the plunger rod to the injection plunger rod position.

Movement of the plunger rod towards the retracted plunger rod position, such as to the retracted plunger rod position, such as after completion of the movement of the plunger rod to the injection plunger rod position, may require that a dwell time has elapsed, e.g. since completion of the movement of the plunger rod to the injection plunger rod position. The dwell time may be chosen to allow sufficient time to ensure that the medicament is distributed into the tissue. The dwell time may be influenced by the medicament and/or concentration of the medicament and/or the amount of medicament. The dwell time may be based on a cartridge specification, e.g. the dwell time may be based on the cartridge code feature, e.g. the dwell time may be based on the code signal.

The processing unit may be configured to control the drive module to move the plunger rod towards the retracted plunger rod position only after the dwell time has elapsed since completion of the movement of the plunger rod to the injection plunger rod position.

The auto injector may comprise a user interface, such as a user interface allowing user input and/or provide visual and/or audible output to the user. The user interface may comprise the first input member, a second input member, the contact member, and/or a first output member. The first output member may be configured to provide output to a user, such as audible and/or visual output. The first output member may comprise an LED and/or a speaker.

The processing unit may be configured to provide one or more user outputs via the user interface. The one or more user outputs may comprise a first user output and/or a second user output. For example, the processing unit may provide the first user output via the first output member.

The processing unit may be configured to provide a user output, e.g. indicative of the injection being complete, via the user interface after the dwell time has elapsed since completion of the movement of the plunger rod to the injection plunger rod position.

The processing unit may be configured to provide a user output indicative of the orientation signal via the user interface. For example, while moving the plunger rod to the mix plunger rod position and/or to the prime plunger rod position. A user output indicative of the orientation signal may comprise a beeping sound with a varying beeping interval based on the orientation signal. For example, the varying beeping interval may be fast when the orientation signal is far away from the predetermined orientation and/or from vertical, and/or the varying beeping interval may be slow when the orientation signal is close to the predetermined orientation and/or vertical.

BRIEF DESCRIPTION OF THE FIGURES

A more detailed description follows below with reference to the drawing, in which.

DETAILED DESCRIPTION

Figure 1:
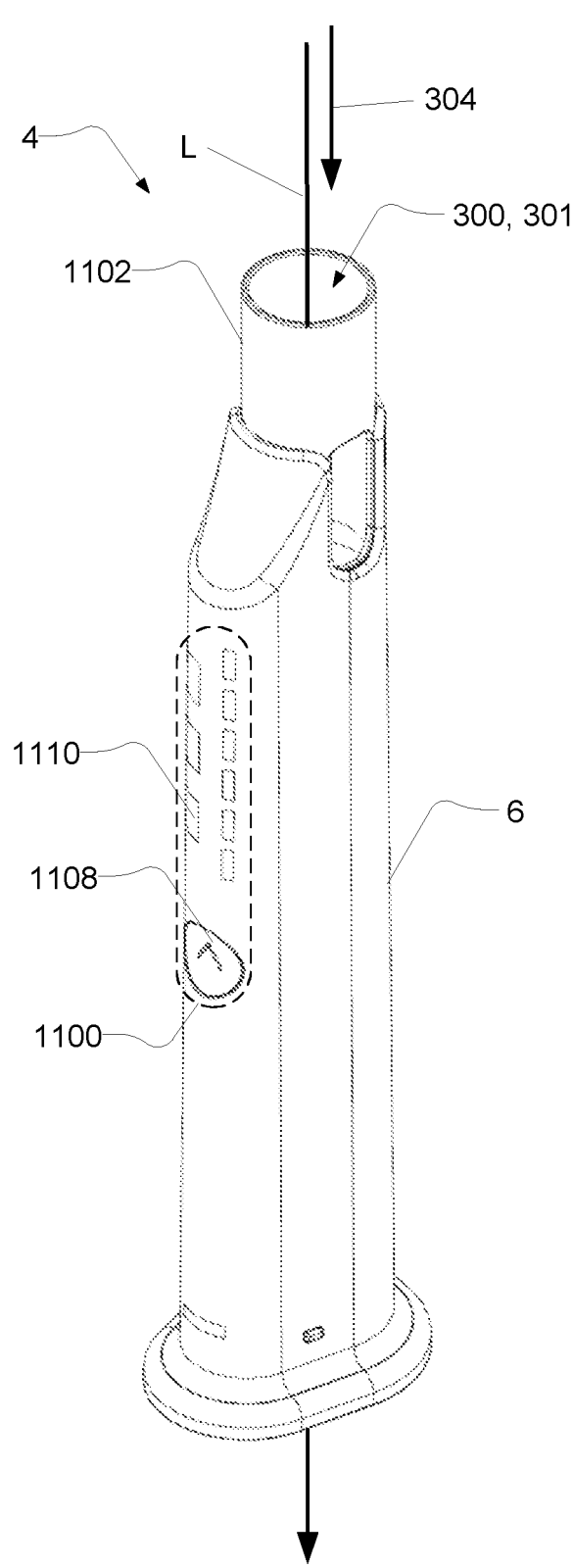
FIG. 1 illustrates an exemplary auto injector.

Various embodiments are described hereinafter with reference to the figures. Like reference numerals refer to like elements throughout. Like elements will, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 illustrates an exemplary auto injector 4. The auto injector 4 may be configured for administering a medicament. The auto injector 4 may be an electronic auto injector.

The auto injector 4 comprises a housing 6. The auto injector 4 comprises a cartridge receiver 300. The cartridge receiver is configured to receive a cartridge and/or a cartridge assembly comprising a cartridge. The cartridge may contain the medicament.

The cartridge receiver 300 has a cartridge receiver opening 301. The cartridge receiver 300 is configured to receive the cartridge and/or the cartridge assembly through the cartridge receiver opening 301 in a cartridge receiving direction 304 along a longitudinal axis L.

The auto injector 4 may comprise a user interface 1100, as illustrated. The auto injector 4 comprises a trigger member, such as the contact member 1102. The contact member 1102 may be configured to be pressed against an injection site. The contact member 1102 may be movable in the cartridge receiving direction 304, relative to the housing, if pressed against the injection site. The contact member 1102 may be part of the user interface 1100.

The user interface 1100 comprises a first input member 1108, e.g. a button. The first input member 1108 may provide for a user input from a user. For example, the first input member 1108 may be used for receiving a push from a user to proceed to a next step.

The user interface 1100 comprises a first output member 1110 as illustrated, e.g. a plurality of LEDs. The first output member 1110 may provide for a user output to a user. The user interface 1100 may comprise a second output member (not shown), e.g. a speaker. The second output member may be configured to provide audible output to the user. For example, the first output member 1110 and/or the second output member may be used to indicate a step in the procedure to the user and/or to indicate an error message.

FIG. 1 illustrates an exemplary auto injector 4. The auto injector 4 may be configured for administering a medicament. The auto injector 4 may be an electronic auto injector.

The auto injector 4 comprises a housing 6. The auto injector 4 comprises a cartridge receiver 300. The cartridge receiver is configured to receive a cartridge and/or a cartridge assembly comprising a cartridge. The cartridge may contain the medicament.

The cartridge receiver 300 has a cartridge receiver opening 301. The cartridge receiver 300 is configured to receive the cartridge and/or the cartridge assembly through the cartridge receiver opening 301 in a cartridge receiving direction 304 along a longitudinal axis L.

The auto injector 4 may comprise a user interface 1100, as illustrated. The auto injector 4 comprises a trigger member, such as the contact member 1102. The contact member 1102 may be configured to be pressed against an injection site. The contact member 1102 may be movable in the cartridge receiving direction 304, relative to the housing, if pressed against the injection site. The contact member 1102 may be part of the user interface 1100.

The user interface 1100 may comprise a first input member 1108 as illustrated, e.g. a button. The first input member 1108 may provide for a user input from a user. For example, the first input member 1108 may be used for receiving a push from a user to proceed to a next step.

The user interface 1100 may comprise a first output member 1110 as illustrated, e.g. a plurality of LEDs. The first output member 1110 may provide for a user output to a user. The user interface 1100 may comprise a second output member (not shown), e.g. a speaker. The second output member may be configured to provide audible output to the user. For example, the first output member 1110 and/or the second output member may be used to indicate a step in the procedure to the user and/or to indicate an error message.

Figure 2:
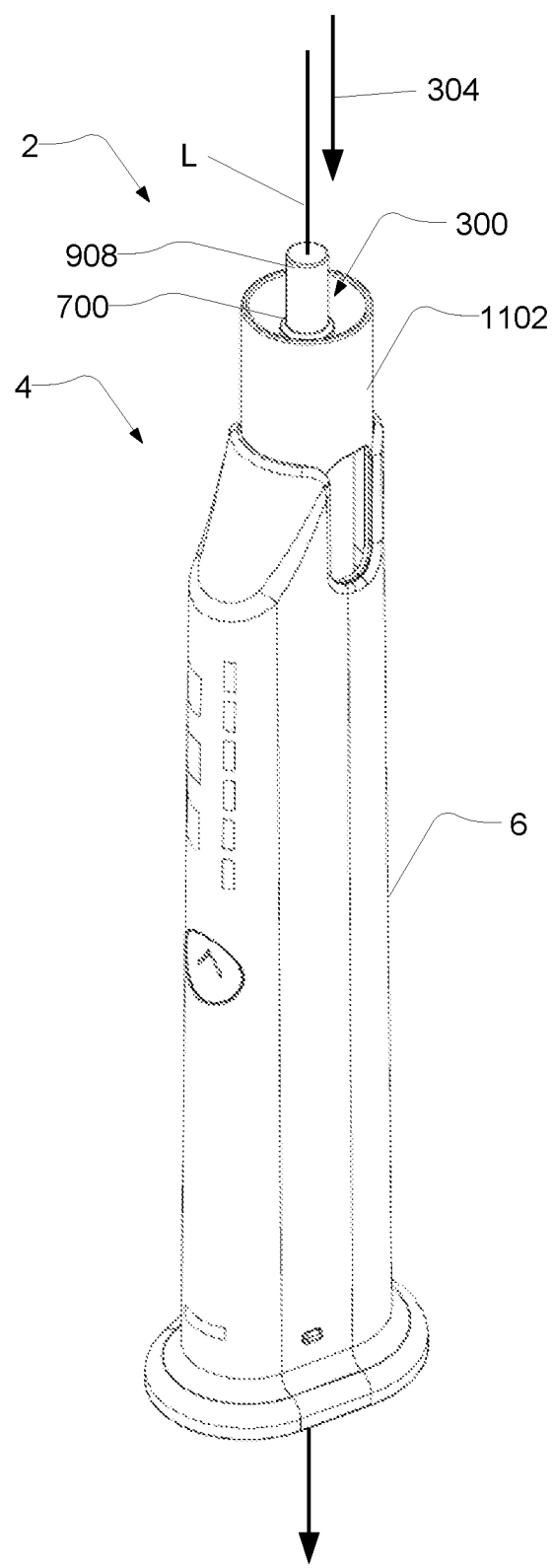
FIG. 2 illustrates an exemplary auto injector with a cartridge.

FIG. 2 illustrates an exemplary system 2. The system 2 comprises an auto injector 4, as described in relation to FIG. 1, and an exemplary cartridge 700 received in the cartridge receiver 300. The cartridge 700 is shown with a needle cover 908. The needle cover 908 extending out of the contact member 1102 to allow removal of the needle cover 908 from the cartridge 700.

Figure 3:
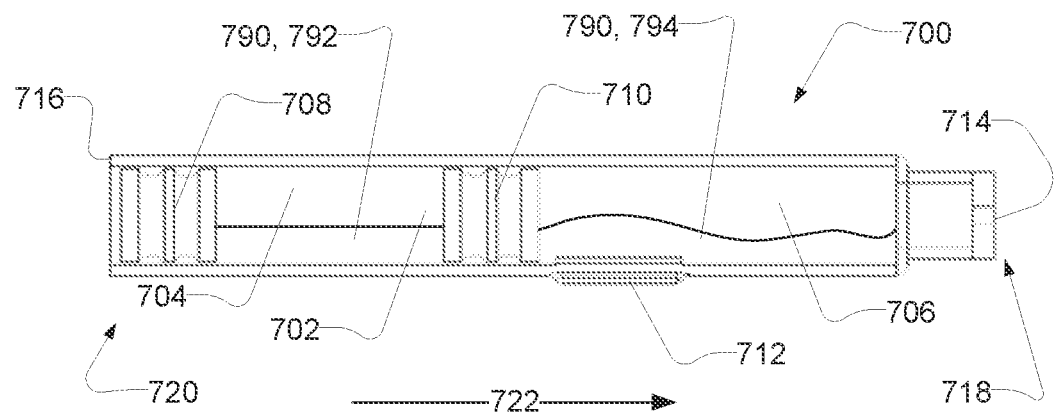
FIG. 3 schematically illustrates an exemplary cartridge.

FIG. 3 schematically illustrates an exemplary cartridge 700, such as a cartridge 700 being configured to be received in the cartridge receiver of an auto injector, such as the auto injector described in relation to previous figures.

The cartridge 700 comprises a cartridge compartment 702. The cartridge compartment 702 may be configured for containing a medicament. The cartridge 700 has a first end 718 and a second end 720. The cartridge 700 comprises a cartridge outlet 714 at the first cartridge end 718. The cartridge may be configured to expel medicament through the cartridge outlet 714.

The cartridge comprises a first stopper 708 movable inside the cartridge compartment, e.g. in a first stopper direction 722, e.g. towards the first cartridge end. For example, the medicament may be expelled through the cartridge outlet 714 upon movement of the first stopper 708 in the first stopper direction. The cartridge comprises a cartridge back face 716 at the second cartridge end. The cartridge back face 716 comprises a cartridge back end opening for providing access to the first stopper 708 for a plunger rod.

As illustrated, the cartridge 700 may be a dual chamber cartridge. The cartridge comprises a second stopper 710 movable inside the cartridge compartment 702, e.g. in the first stopper direction 722, e.g. towards the first cartridge end. The cartridge compartment 702 comprises a first cartridge subcompartment 704 and a second cartridge subcompartment 706. The first cartridge subcompartment 704 is between the first stopper 708 and the second stopper 710. The second cartridge subcompartment 706 is between the second stopper 710 and the cartridge outlet 714. The cartridge comprises a bypass section 712 for providing fluid communication between the first cartridge subcompartment and the second cartridge subcompartment. The bypass section 712 provides fluid communication between the first cartridge subcompartment and the second cartridge subcompartment when the second stopper 710 is positioned in the bypass section 712.

The first cartridge subcompartment 704 contains a first medicament component 792 of the medicament 790. The first medicament component 792 may be a liquid as illustrated. The second cartridge subcompartment 706 contains a second medicament component 794 of the medicament 790. The second medicament component 794 may be a powder composition. By positioning of the second stopper 710 within the bypass section 712, the first medicament component 792 may be transmitted into the second cartridge subcompartment 706 via the bypass section 712, thereby mixing the first medicament component 792 and the second medicament component 794 to achieve the combined medicament 790.

FIGS. 4A, 4B, 4C, and 4D schematically illustrates an exemplary cartridge assembly 600. The cartridge assembly 600 comprises an exemplary cartridge 700 and an exemplary cartridge code feature 1000. The cartridge 700 has a first cartridge end 718 and a second cartridge end 720. The first stopper direction 722 is from the second cartridge end 720 to the first cartridge first 718. The cartridge code feature 1000 is positioned near the second cartridge end 720, e.g. closer to the second cartridge end 720 than the first cartridge end 718. In another exemplary cartridge assembly, the cartridge code feature 1000 may be positioned near the first cartridge end 718.

FIGS. 4A, 4B, 4C, and 4D illustrates different types of exemplary cartridge code features 1000.

Figures 4A, 4B, 4C, 4D:
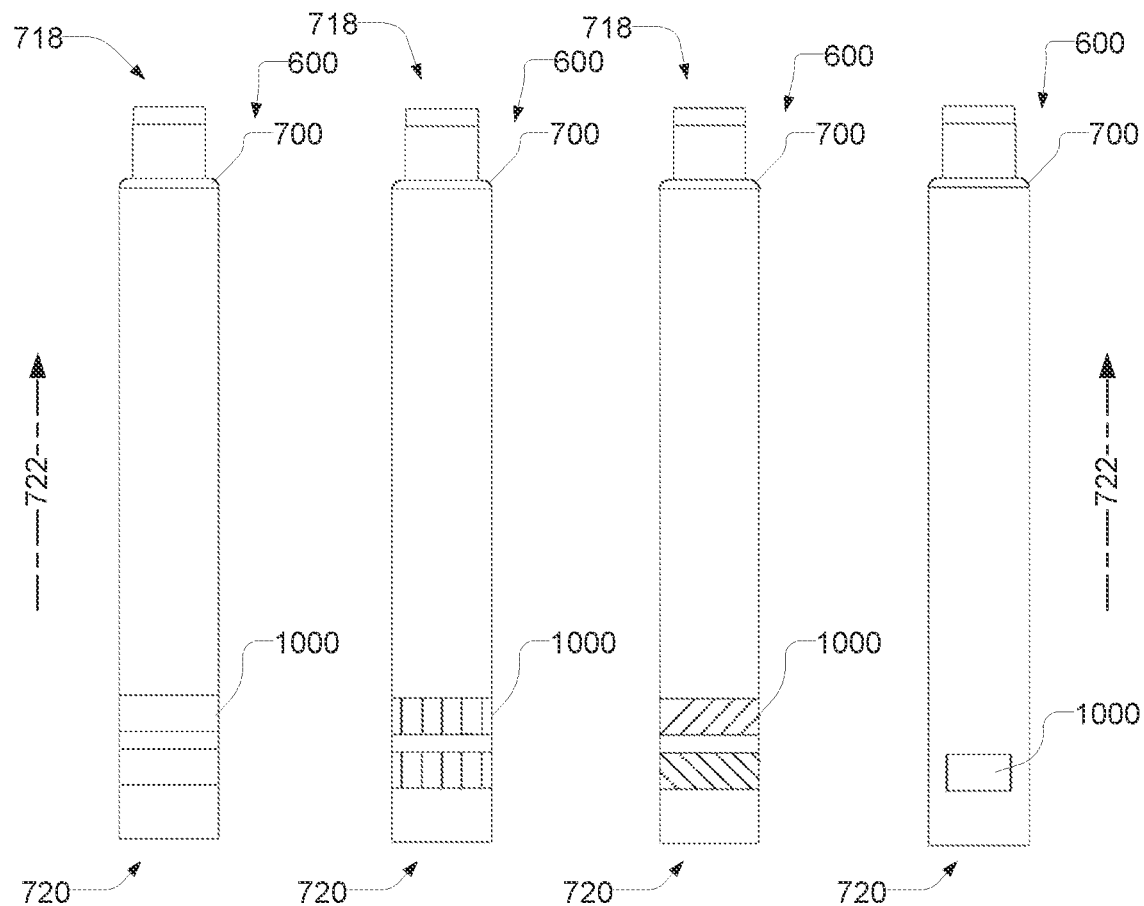
FIGS. 4A, 4B, 4C and 4D schematically illustrate an exemplary cartridge assembly with exemplary cartridge code features.

FIG. 4A illustrates an exemplary cartridge assembly 600, wherein the cartridge code feature 1000 comprises two strips. The two strips may be coloured, e.g. differently coloured. The combination and/or sequence of colours may be indicative of a code of the cartridge code feature 1000.

FIG. 4B illustrates an exemplary cartridge assembly 600, wherein the cartridge code feature 1000 comprises bar codes. The cartridge code feature 1000 may comprise one or more bar codes. The bar code may be indicative of a number indicative of a code of the cartridge code feature 1000.

FIG. 4C illustrates an exemplary cartridge assembly 600, wherein the cartridge code feature 1000 comprises differently grated strips. For example, as illustrated, the cartridge code feature 1000 may comprise two strips wherein the first strip is grated at 45 deg., and the second strip is grated at −45 deg. The grating, and/or the grating of the strips relative to each other, may be indicative of a code of the cartridge code feature 1000.

FIG. 4D illustrates an exemplary cartridge assembly 600, wherein the cartridge code feature 1000 comprises an electromagnetically readable tag, such as an RFID tag or an NFC tag. The electromagnetically readable tag may contain data that is indicative of a code of the cartridge code feature 1000.

Figure 5:
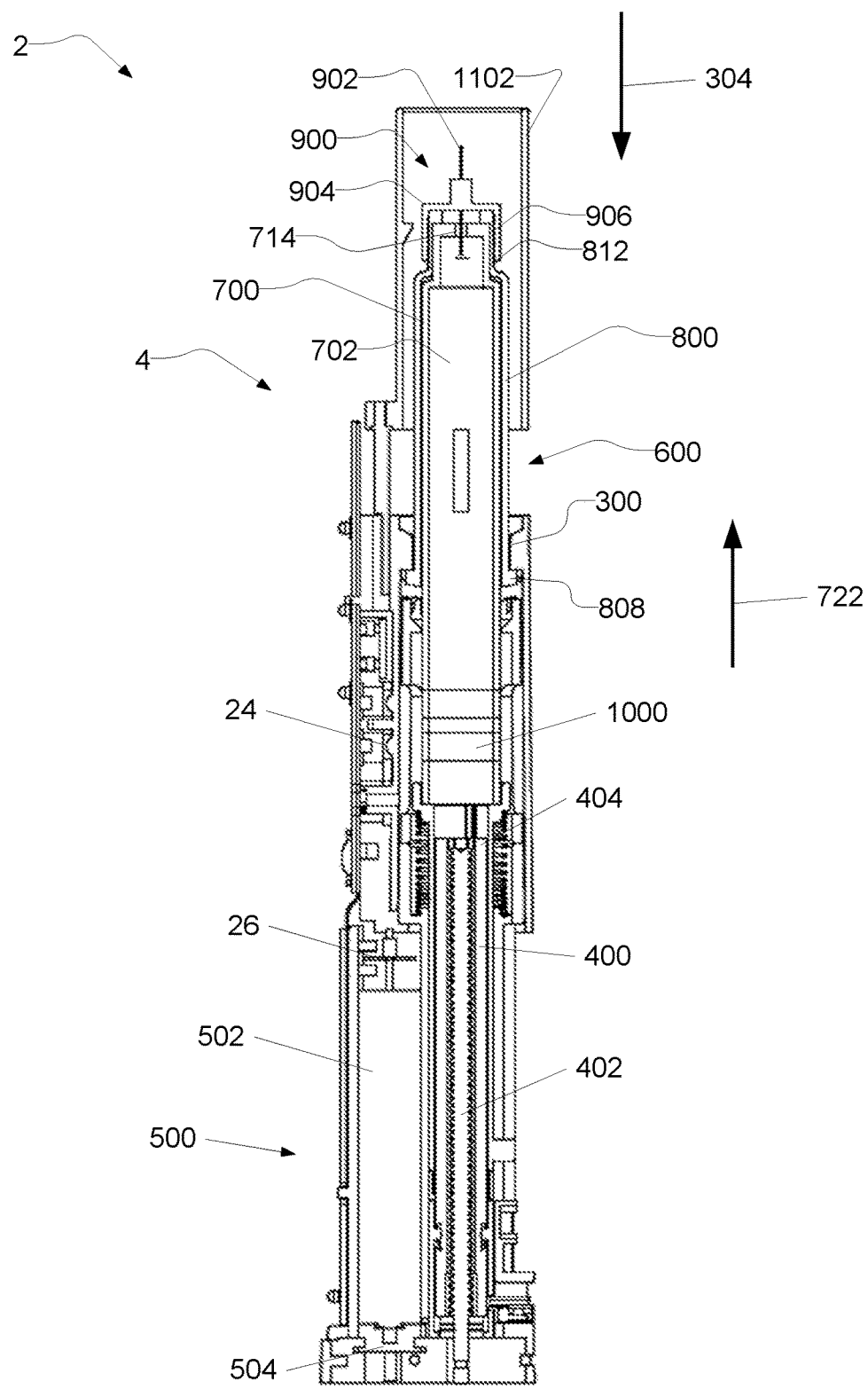
FIG. 5 schematically illustrates an exemplary auto injector with a cartridge assembly.

FIG. 5 illustrates an exemplary system 2. The system 2 comprises an auto injector 4, as described, for example, in relation to FIG. 1, and an exemplary cartridge assembly 600. The cartridge assembly 600 comprises a cartridge 700 with a cartridge compartment 702, a needle assembly 900, and a cartridge code feature 1000. The cartridge assembly 600 is received in the auto injector 4.

The cartridge assembly 600 comprises a cartridge holder 800. The cartridge holder 800 is configured for retention of the cartridge 700 in the cartridge receiver 300 of the auto injector 4. The cartridge holder 800 comprises a cartridge retention member 808. The cartridge retention member 808 engages with the cartridge receiver 300 for reception and retention of the cartridge 700 and the cartridge assembly 600 in the cartridge receiver 300.

The needle assembly 900 comprises a needle 902 and a needle hub 904. The needle assembly 900 is attached to the cartridge 700, e.g. by the needle hub 904 having a cartridge holder coupling portion 906, e.g. a threaded coupling portion, being in engagement with a needle assembly coupling portion 812 of the cartridge holder 800. The needle 902 extends through the cartridge outlet 714 of the cartridge 700. The cartridge outlet 714 may be blocked by a resilient sealing being penetrated by the needle 902, when the needle assembly 900 is attached to the cartridge 700.

The auto injector 4 comprises a code sensor 24 configured to read the cartridge code feature 1000. When the cartridge assembly 600 is inserted, as shown, the cartridge code feature 1000 is lined up with the code sensor 24.

The auto injector 4 comprises a plunger rod 400. The plunger rod 400 is configured to advance a first stopper of the cartridge 700. The plunger rod 400 comprises an outer plunger rod 404 with an inner thread, and an inner plunger rod 402 with an outer thread. The thread of the inner plunger rod 402 is in engagement with the thread of the outer plunger rod 404. The outer plunger rod 404 is prevented from rotating relative to the housing of the auto injector. The movement of the plunger rod 400 comprises rotation of the inner plunger rod 402. The rotation of the inner plunger rod 402 results in translational movement of the outer plunger rod 404, due to the outer plunger rod 404 being rotationally restricted. The outer plunger rod 404, when moved translationally in the first stopper direction 722, is configured to abut the first stopper of the cartridge 700, and to move the first stopper in the first stopper direction 722.

The drive module 500 is coupled to actuate the plunger rod 400. The drive module 500 is electrically connected to a battery for receiving electrical power. The drive module 500 comprises a motor 502, such as an electro-mechanical motor, such as a DC motor. The drive module 500 comprises a transmission 504 for coupling the motor 502 to the inner plunger rod 402 of the plunger rod 400.

Although the example shown comprises a motor 502, which may be an electro-mechanical motor, it will be readily understood that the auto injector 4 may be realised having an alternative drive module, such as comprising a solenoid motor, a shape memory metal engine, an arrangement of springs and/or a pressurized gas configured to actuate the plunger rod 400.

The auto injector 4 comprises an ejection sensor 26, such as a plunger rod position sensor. The ejection sensor 26 is configured to detect the position of the plunger rod 400. In the illustrated example, the ejection sensor 26 comprises a tachometer configured to count/detect the revolutions of the motor 502. Thus, the position of the plunger rod 400 may be determined based on the count of revolutions of the motor 502. The ejection sensor 26 may, based on the detection of the position of the plunger rod 400, detect the expelling of medicament and/or air in the cartridge compartment. The position of the plunger rod 400 may be indicative of the position of the first stopper of the cartridge 700, e.g. the most advanced position of the plunger rod 400, e.g. while the cartridge 700 is in the cartridge receiver 300, may be indicative of the position of the first stopper of the cartridge 700.

FIGS. 6A, 6B, 6C, and 6D schematically illustrate an auto injector 4 and a cartridge assembly 600. FIGS. 6A, 6B, 6C, and 6D schematically illustrates exemplary positions of a contact member 1102 of the auto injector 4 in various situations.

The auto injector 4 comprises a cartridge receiver 300 configured for receiving and retaining a cartridge. The auto injector 4 comprises a contact member 1102. The contact member 1102 may be movable between an extended contact member position and a retracted contact member position. The contact member 1102 comprises a contact member protruding part 1112. The contact member protruding part 1112 is configured to move with the contact member 1102.

The contact member 1102 may be biased, e.g. by a contact member spring (not shown), towards the extended contact member position.

The contact member comprises a needle cover engagement member 1114. The needle cover engagement member 1114 is configured to abut a needle cover abutment face, e.g. of a needle cover positioned on the cartridge inserted into the cartridge receiver 300.

The auto injector 4 comprises a contact member sensor 1104 configured to detect a position of the contact member 1102. The contact member sensor 1104 comprises a first contact member sensor 1130 and a second contact member sensor 1132. The first contact member sensor 1130 and the second contact member sensor 1132 may be optical sensors. The contact member sensor 1104 detects the position of the contact member 1102 by the contact member protruding part 1112 covering the first contact member sensor 1130 when the contact member 1102 is in a first contact member position, and the contact member protruding part 1112 covering the second contact member sensor 1132 when the contact member 1102 is in a second contact member position.

The first contact member position may be detected by the first contact member sensor 1130 being covered and the second contact member sensor 1132 being covered. The second contact member position may be detected by the first contact member sensor 1130 not being covered and the second contact member sensor 1132 being covered. The extended contact member position may be detected by the first contact member sensor 1130 not being covered and the second contact member sensor 1132 not being covered.

Figure 6A:
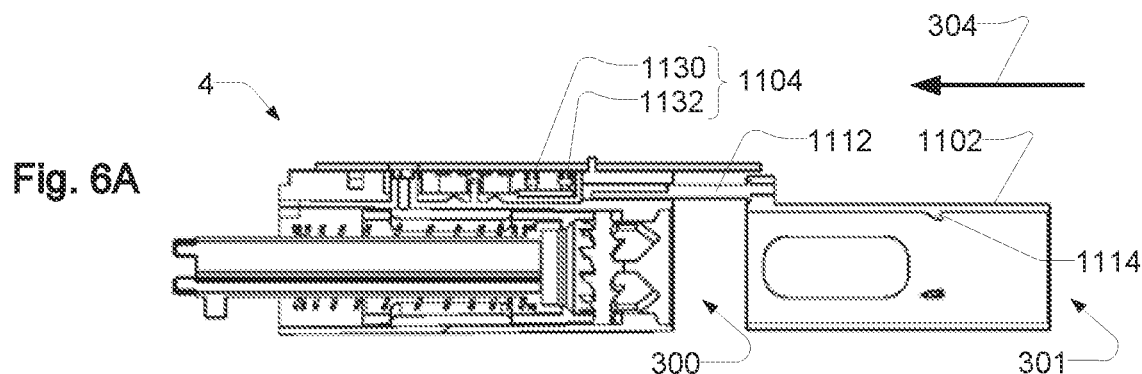
FIGS. 6A, 6B, 6C, and 6D schematically illustrate an auto injector and a cartridge assembly.

FIG. 6A schematically illustrates the auto injector 4 with no received cartridge and/or cartridge assembly. The contact member 1102 is in the extended contact member position. A cartridge may be inserted into the cartridge receiver 300 in the cartridge receiving direction 304 through the contact member 1102 defining a cartridge receiver opening 301.

Figure 6B:
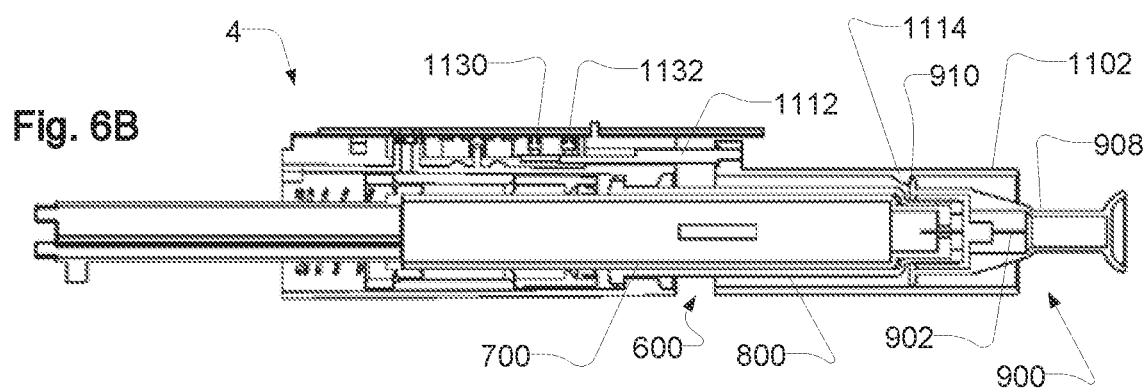

FIG. 6B schematically illustrates the auto injector 4 with a cartridge assembly 600 received. The cartridge assembly 600 comprises a cartridge 700, a cartridge holder 800 and a needle assembly 900. The needle assembly comprises a needle 902 and a needle cover 908. The needle cover has a needle cover abutment face 910. The needle cover abutment face 910 engages the needle cover engagement member 1114 of the contact member 1102. The contact member 1102 is in the second contact member position, e.g. caused by the presence of the needle cover 908 and the abutment of the needle cover abutment face 910 on the needle cover engagement member 1114. The contact member protruding part 1112 covers the second contact member sensor 1132. The contact member protruding part 1112 does not cover the first contact member sensor 1130.

Figure 6C:
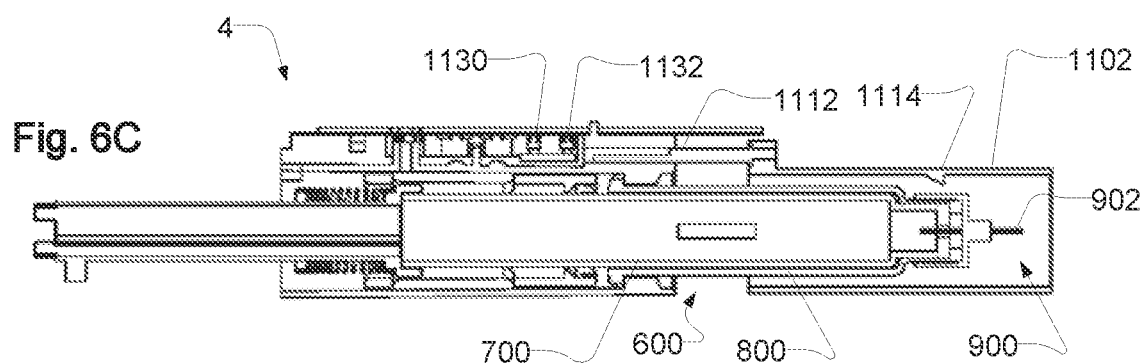

FIG. 6C schematically illustrates the auto injector 4 with a cartridge assembly 600 received. Compared to FIG. 6B, the needle cover 908 has been removed. The contact member 1102 is in the extended contact member position. The contact member 1102 is allowed to be moved to the extended contact member position since the needle cover abutment face 910 does not abut the needle cover engagement member 1114. The contact member protruding part 1112 has moved with the contact member 1102. The contact member protruding part 1112 does not cover the second contact member sensor 1132. The contact member protruding part 1112 does not cover the first contact member sensor 1130.

Figure 6D:
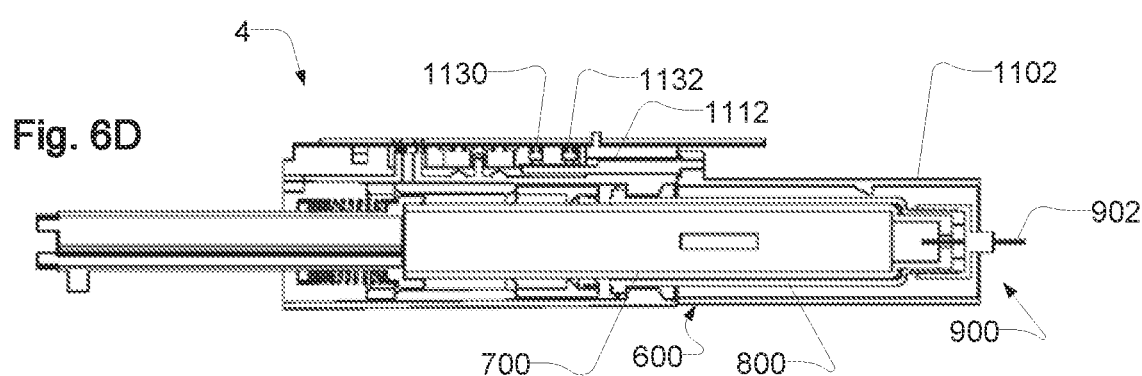

FIG. 6D schematically illustrates the auto injector 4 with a cartridge assembly 600 received. The contact member 1102 is in the first contact member position. The first contact member position may be the retracted contact member position, or close to the retracted contact member position. The contact member 1102 may have been moved to the first contact member position by the contact member 1102 being pressed against an injection site, thereby inserting the needle 902 into the injection site. The contact member protruding part 1112 has moved with the contact member 1102. The contact member protruding part 1112 covers the first contact member sensor 1130. The contact member protruding part 1112 covers the second contact member sensor 1132.

Figure 7:
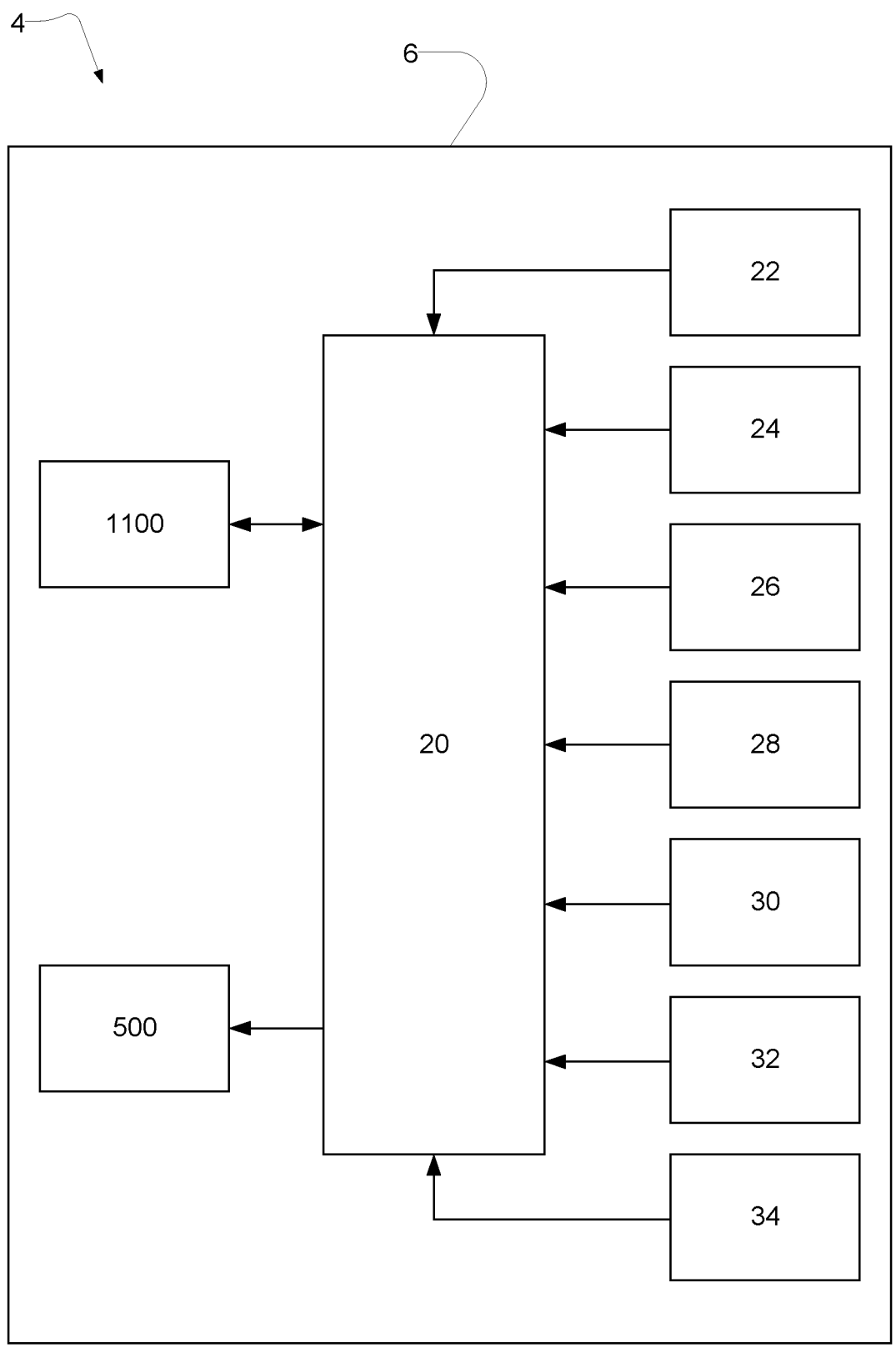
FIG. 7 shows a block diagram of an exemplary auto injector.

FIG. 7 shows a block diagram of an exemplary auto injector 4. The auto injector 4 comprises a plurality of sensors 22, 24, 26, 28, 30, 32, 34, a processing unit 20, a drive module 500, and a user interface 1100. The sensors 22, 24, 26, 28, 30, 32, 34 are coupled to the processing unit 20. The user interface 1100 is coupled to the processing unit 20. The processing unit is coupled to the drive module 500.

The processing unit 20 receives signals from the sensors 22, 24, 26, 28, 30, 32, 34 and the user interface 1100. The processing unit 20 is configured to control the drive module 500. The processing unit 20 may control the drive module 500 based on one or more of the received signals from the sensors 22, 24, 26, 28, 30, 32, 34 and the user interface 1100. The processing unit 20 is configured to provide user outputs via the user interface 1100.

The auto injector 4 comprises an orientation sensor 22. The orientation sensor 22 is configured to provide an orientation signal indicative of the orientation of a cartridge received in the auto injector 4. For example, the orientation sensor 22 may be configured to detect the orientation of the auto injector 4. The orientation of the cartridge may be determined based on the orientation of the auto injector 4. The orientation sensor 22 may be configured to detect the direction of gravity. For example, the orientation sensor 22 may comprise an accelerometer.

The processing unit 20 is coupled to the orientation sensor 22. The processing unit 20 is configured to receive the orientation signal. The processing unit 20 may determine the orientation of the cartridge based on the orientation signal. The processing unit 20 may control the drive module 500 based on the orientation signal. For example, the processing unit 20 may be configured to control the drive module 500 to move the plunger rod based on the orientation signal. For example, the processing unit 20 may be configured to control the drive module 500 to move the plunger rod towards the extended plunger rod position, such as to a pre-mix plunger rod position and/or a mix plunger rod position and/or the prime plunger rod position, only if the cartridge outlet is pointing upwards. Alternatively or additionally, the processing unit 20 may provide user output via the user interface 1100 based on the orientation signal.

The auto injector 4 comprises a code sensor 24. The code sensor 24 is configured to read a cartridge code feature, and provide a code signal indicative of a cartridge code feature. For example, the code sensor may be configured to read/detect a colour code.

The processing unit 20 is coupled to the code sensor 24. The processing unit 20 is configured to receive the code signal. The processing unit 20 may determine the cartridge code feature of the cartridge assembly based on the code signal. The processing unit 20 may control the drive module 500 based on the code signal. For example, the processing unit 20 may be configured to control the drive module 500 to move the plunger rod towards the extended plunger rod position, such as to the pre-mix plunger rod position and/or the mix plunger rod position and/or the prime plunger rod position and/or the injection plunger rod position, based on the code signal. The processing unit 20 may be configured to determine a threshold, such as a plunger rod threshold, and/or a resistance threshold, based on the code signal. Alternatively or additionally, the processing unit 20 may provide user output via the user interface 1100 based on the code signal.

The auto injector 4 comprises an ejection sensor 26, such as a plunger rod position sensor. The ejection sensor 26 is configured to detect the position of the plunger rod of the auto injector 4, and provide an ejection sensor signal indicative of the position of the plunger rod. The ejection sensor 26 may comprise a tachometer coupled to the drive module 500.

The processing unit 20 is coupled to the ejection sensor 26. The processing unit 20 is configured to receive the ejection sensor signal. The processing unit 20 may determine the position of the plunger rod based on the ejection sensor signal. The processing unit 20 may control the drive module 500 based on the ejection sensor signal. For example, the processing unit 20 may be configured to control the drive module 500 to start, stop or continue movement of the plunger rod based on the ejection sensor signal. For example, the processing unit 20 may be configured to determine a present plunger rod position based on the ejection sensor signal. The plunger rod being in the pre-mix plunger rod position and/or the mix plunger rod position and/or the prime plunger rod position and/or the injection plunger rod position may be determined based on the ejection sensor signal. Alternatively or additionally, the processing unit 20 may provide user output via the user interface 1100 based on the ejection sensor signal.

The auto injector 4 comprises a cartridge sensor 28. The cartridge sensor 28 is configured to detect reception of a cartridge assembly in the auto injector 4. The cartridge sensor 28 provides a cartridge sensor signal indicative of reception of a cartridge assembly.

The processing unit 20 is coupled to the cartridge sensor 28. The processing unit 20 is configured to receive the cartridge sensor signal. The processing unit 20 may control the drive module 500 based on the cartridge sensor signal. For example, the processing unit 20 may be configured to control the drive module 500 to start movement of the plunger rod if a cartridge assembly is received, and/or only if a cartridge assembly is received. Alternatively or additionally, the processing unit 20 may provide user output via the user interface 1100 based on the cartridge sensor signal.

The code sensor 24 and the cartridge sensor 28 may be the same sensor, e.g. the code sensor 24 may be configured to detect reception of a cartridge assembly and subsequently read the cartridge code feature.

The auto injector 4 comprises a needle sensor 30. The needle sensor 30 is configured to detect a needle, and/or a needle assembly, and/or a needle cover of a needle assembly, of the cartridge assembly, when the cartridge assembly is received in the auto injector 4. The needle sensor 30 provides a needle signal indicative of the presence of a needle, and/or a needle assembly, and/or a needle cover of a needle assembly, of the cartridge assembly.

The processing unit 20 is coupled to the needle sensor 30. The processing unit 20 is configured to receive the needle signal. The processing unit 20 may control the drive module 500 based on the needle signal. For example, the processing unit 20 may be configured to control the drive module 500 to start movement of the plunger rod, e.g. towards the extended plunger rod position, such as to the pre-mix plunger rod position and/or the mix plunger rod position and/or the prime plunger rod position and/or the injection plunger rod position, only if a needle is present, and/or only if a needle cover is not present, such as removed. Detection of a needle cover may be indicative of a needle being present. The processing unit 20 may be configured to control the drive module 500 to start only if a needle cover has been detected, and subsequently is not detected, e.g. it has been removed. Alternatively or additionally, the processing unit 20 may provide user output via the user interface 1100 based on the needle signal.

The needle sensor 30 may be part of the contact member sensor, as exemplified in FIGS. 6A, 6B, 6C, and 6D.

The auto injector 4 comprises a temperature sensor 32. The temperature sensor 32 is configured to detect a temperature, such as a temperature of the auto injector and/or of the cartridge and/or of the medicament. The temperature sensor 32 is configured to provide a temperature signal indicative of the temperature.

The processing unit 20 is coupled to the temperature sensor 32. The processing unit 20 is configured to receive the temperature signal. The processing unit 20 may be configured to determine the temperature, such as the temperature of the auto injector and/or of the cartridge and/or of the medicament based on the temperature signal. The processing unit 20 may control the drive module 500 based on the temperature signal. For example, the processing unit 20 may be configured to control the drive module 500 to move the plunger rod towards the extended plunger rod position, such as to the pre-mix plunger rod position and/or the mix plunger rod position and/or the prime plunger rod position and/or the injection plunger rod position, based on the temperature signal. The processing unit 20 may determine plunger rod positions based on the temperature signal. For example, the processing unit 20 may be configured to determine the pre-mix plunger rod position and/or the mix plunger rod position and/or the prime plunger rod position and/or the injection plunger rod position based on the temperature signal. Alternatively or additionally, the processing unit 20 may provide user output via the user interface 1100 based on the temperature signal.

The auto injector 4 comprises a resistance sensor 34. The resistance sensor 34 is configured to detect resistance against movement of the plunger rod of the auto injector 4. The resistance sensor 34 may be configured to detect resistance against movement of the plunger rod based on measurements of the drive module 500. For example, the resistance sensor 34 may be configured to detect the electrical current of a motor of the drive module 500. The resistance sensor 34 is configured to provide a resistance signal indicative of resistance against movement of the plunger rod.

The processing unit 20 is coupled to the resistance sensor 34. The processing unit 20 is configured to receive the resistance signal. The processing unit 20 may be configured to determine the resistance against movement of the plunger rod based on the resistance signal. The processing unit 20 may control the drive module 500 based on the resistance signal. For example, the processing unit 20 may be configured to control the drive module 500 to adjust movement of the plunger rod based on the resistance signal. For example, the processing unit 20 may be configured to control the drive module 500 to start, stop or continue movement of the plunger rod based on the resistance signal. Alternatively or additionally, the processing unit 20 may provide user output via the user interface 1100 based on the resistance signal.

The auto injector 4 is illustrated comprising all of the above mentioned sensors. However, alternatively, the auto injector may comprise only one or any combination of one or more of the above mentioned sensors.

The auto injector comprises a user interface 1100. The user interface 1100 may comprise one or more input members, e.g. a first input member, for receiving a user input. The user interface is configured to provide a user input signal indicative of the received user input. The user interface 1100 may provide a first input signal and/or a second input signal.

The processing unit 20 is coupled to the user interface 1100. The processing unit 20 is configured to receive the user input signal, such as the first input signal and/or the second input signal. The processing unit 20 may control the drive module 500 based on the user input signal. For example, the processing unit 20 may be configured to control the drive module 500 to move the plunger rod towards the extended plunger rod position, such as to the pre-mix plunger rod position and/or the mix plunger rod position and/or the prime plunger rod position and/or the injection plunger rod, based on the user input signal and/or following the user input signal.

The auto injector comprises a housing 6 accommodating the sensors 22, 24, 26, 28, 30, 32, 34, processing unit 20, user interface 1100 and drive module 500.

FIGS. 8A, 8B, 8C, 8D, 8E, and 8F schematically illustrate exemplary cartridge assemblies 600 and a plunger rod 400. The cartridge assembly 600 comprises a cartridge 700, such as the cartridge described in relation to FIG. 3, a cartridge holder 800, and a needle assembly 900. For intelligibility, the auto injector comprising the plunger rod 400 is not shown.

The cartridge holder 800 comprises a cartridge retention member 808. The cartridge retention member 808 is configured for engagement with a cartridge receiver of the auto injector. The cartridge holder 800 comprises a needle assembly coupling portion 812. The needle assembly coupling portion 812 is configured for engagement with a cartridge holder coupling portion 906 of the needle assembly 900. The needle assembly coupling portion 812 allows attachment of a needle to the cartridge 700.

The needle assembly 900 comprises a needle 902 and a needle hub 904. The needle assembly 900 is attached to the cartridge 700, e.g. by the needle hub 904 having a cartridge holder coupling portion 906, e.g. a threaded coupling portion, being in engagement with a needle assembly coupling portion 812 of the cartridge holder 800. The needle 902 extends through the cartridge outlet 714 of the cartridge 700.

Figure 8A:
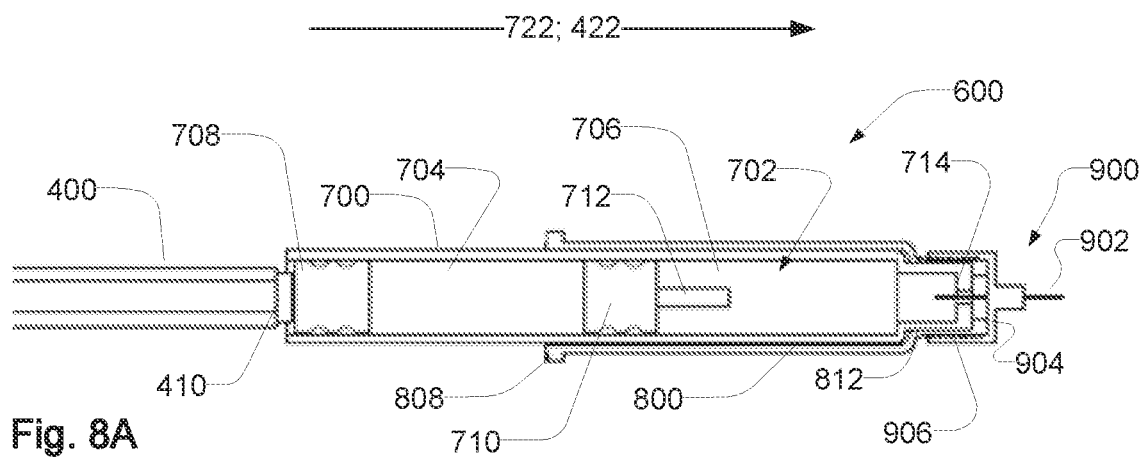
FIGS. 8A, 8B, 8C, 8D, 8E, and 8F schematically illustrate an exemplary cartridge assembly and a plunger rod in exemplary positions.

FIG. 8A schematically illustrates a situation wherein the plunger rod 400 is in an exemplary retracted plunger rod position. The cartridge 700 may be a new cartridge. The first stopper 708 is positioned in an initial position. The second stopper 710 is in an initial position, e.g. behind the bypass section 712, wherein the bypass section 712 does not form a fluid connection between the first subcompartment 704 and the second subcompartment 706.

Figure 8B:
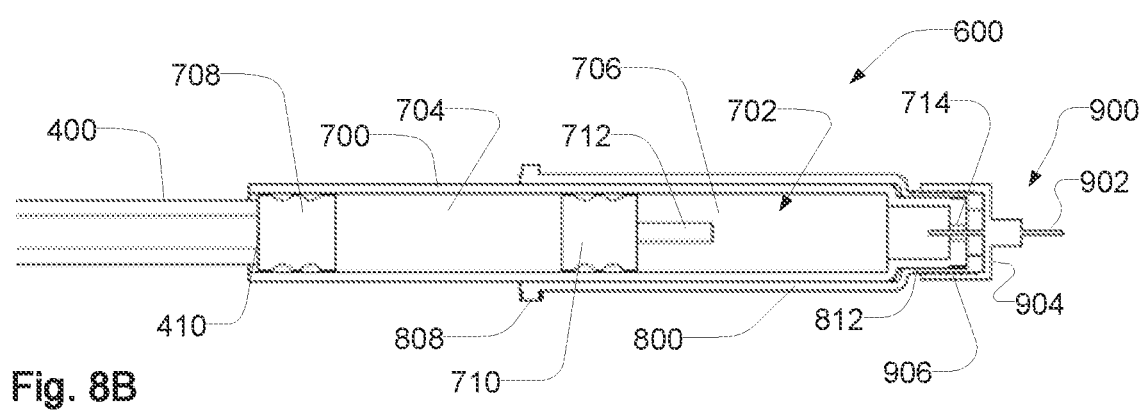

FIG. 8B schematically illustrates a situation wherein the plunger rod 400 is in an exemplary pre-mix plunger rod position. Compared to FIG. 8A, the plunger rod 400 is moved towards an extended plunger rod position. A plunger rod front end 410 of the plunger rod 400 abuts the first stopper 708. Thus, the plunger rod 400 has started to move the first stopper 708 in the first stopper direction 722, by movement in the first plunger rod direction 422. The second stopper 710 is in a position, e.g. behind the bypass section 712, wherein the bypass section 712 does not form a fluid connection between the first subcompartment 704 and the second subcompartment 706.

Figure 8C:
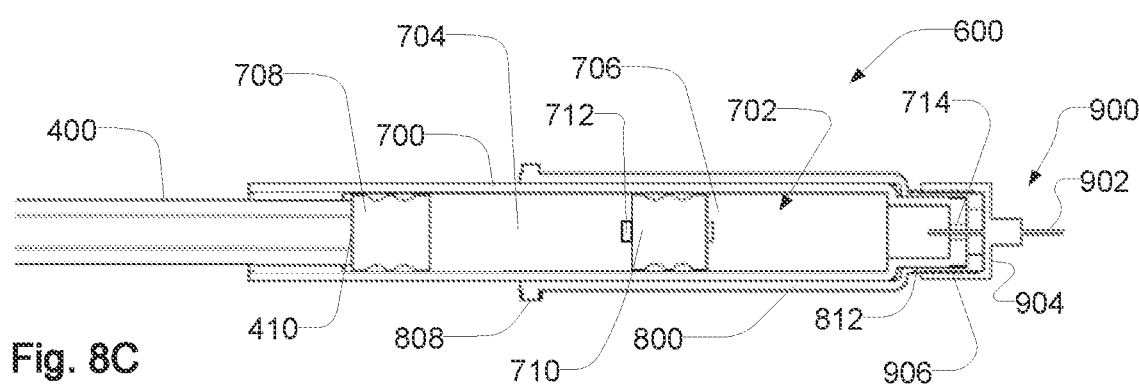

FIG. 8C schematically illustrates a situation wherein the plunger rod 400 is in an exemplary position wherein a fluid connection is established between the first subcompartment 704 and the second subcompartment 706 via the bypass section 712. The plunger rod front end 410 of the plunger rod 400 abuts the first stopper 708. The plunger rod 400 has moved the first stopper 708 in the first stopper direction 722, by movement in the first plunger rod direction 422. The second stopper 710 is in the bypass section 712, wherein the bypass section 712 forms a fluid connection between the first subcompartment 704 and the second subcompartment 706. Thus, further movement of the first stopper 708 in the first stopper direction 722, e.g. by movement of the plunger rod 400 in the first plunger rod direction 422, will transmit the content of the first subcompartment 704, e.g. a first medicament component (not shown) into the second subcompartment 706, e.g. through the bypass section 712.

Figure 8D:
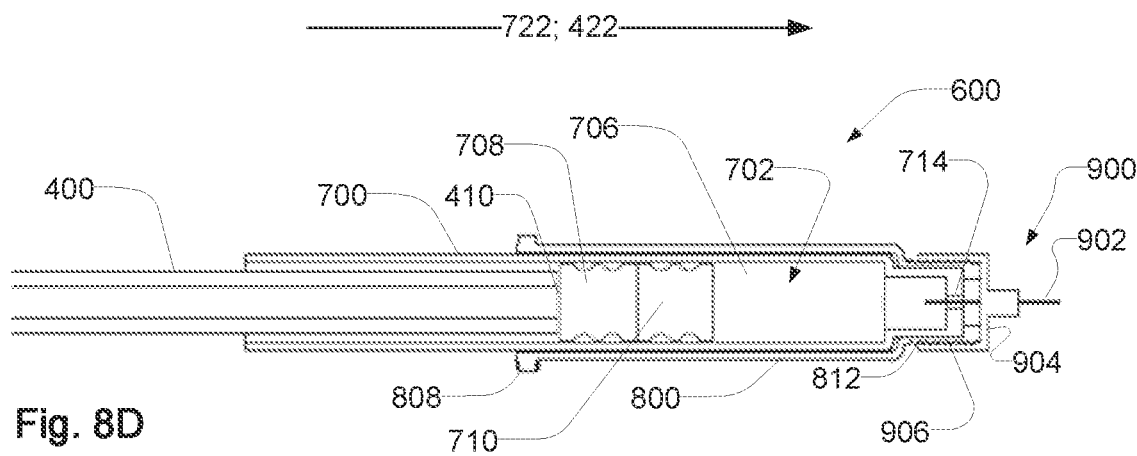

FIG. 8D schematically illustrates a situation wherein the plunger rod 400 is in an exemplary mix plunger rod position. The plunger rod front end 410 abuts the first stopper 708. The first stopper 708 abuts the second stopper 710. The first subcompartment 704 is compressed. The second stopper 710 is in a position after the bypass section 712. Thus, the fluid connection between the first subcompartment 704 and the second subcompartment 706 has been closed.

Figure 8E:
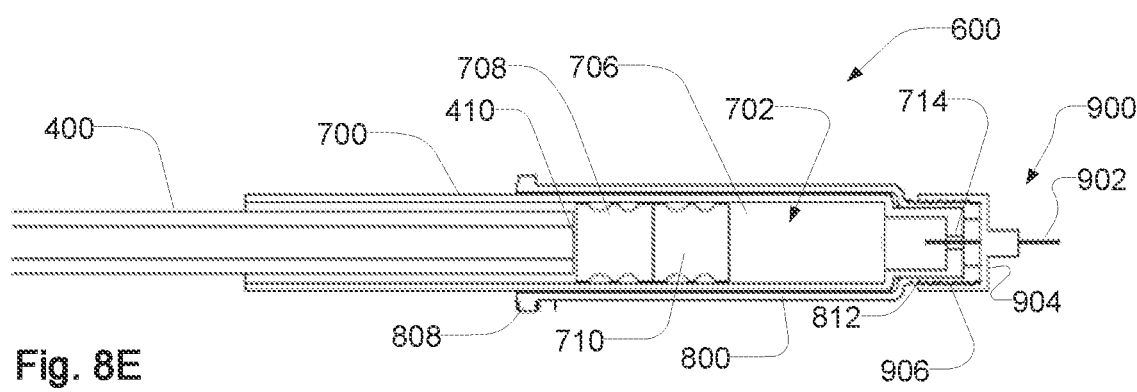

FIG. 8E schematically illustrates a situation wherein the plunger rod 400 is in an exemplary prime plunger rod position. Compared to FIG. 8D, the plunger rod 400 is moved towards an extended plunger rod position, e.g. to expel air from the cartridge compartment 702.

Figure 8F:
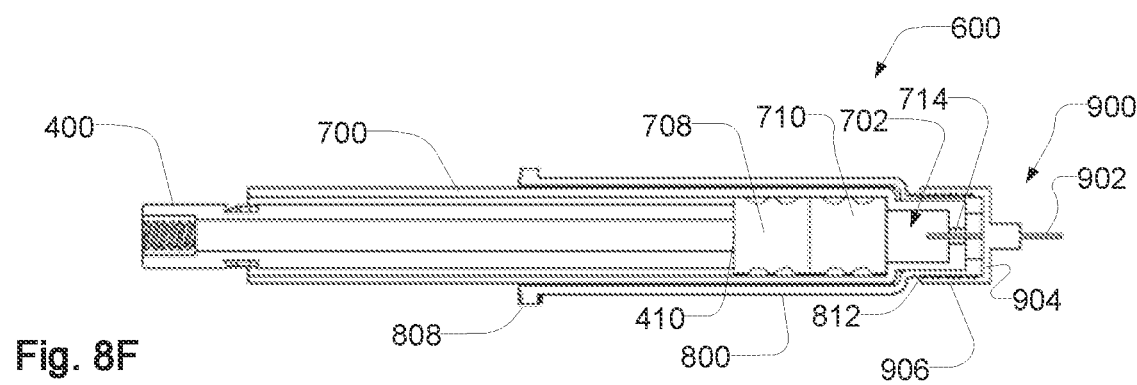

FIG. 8F schematically illustrates a situation wherein the plunger rod 400 is in an exemplary injection plunger rod position. For example after complete injection, the plunger rod 400 may be in the injection plunger rod position. The first stopper 708 and the second stopper 710 is in a position close to the cartridge outlet 714. Contents of the cartridge component, e.g. the medicament, has been expelled, e.g. through the cartridge outlet 714 and/or the needle 902. A residual volume of the medicament may be remaining in the cartridge.

Figure 9:
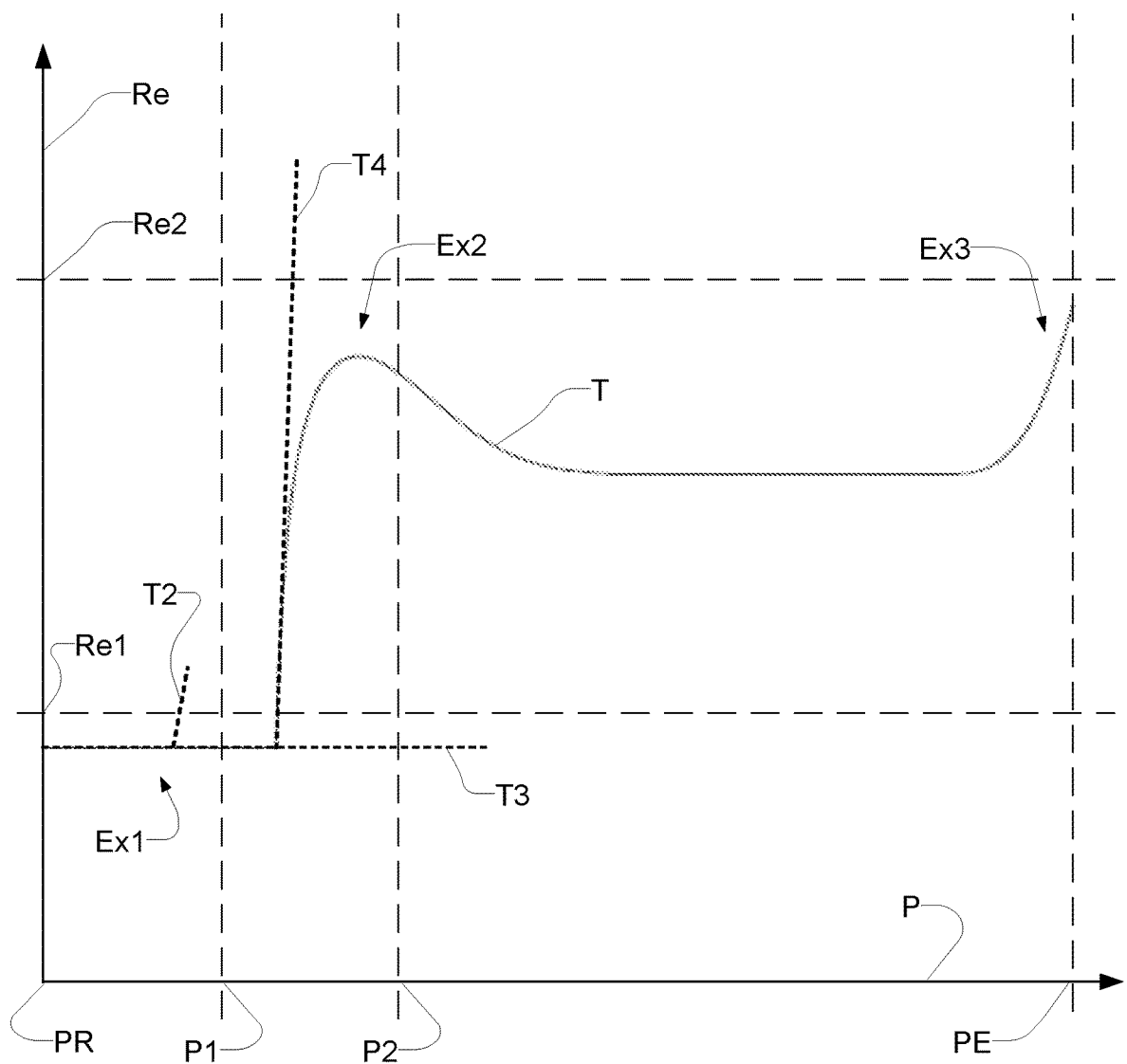
FIG. 9 shows an exemplary graph of resistance vs. position.

FIG. 9 shows an exemplary trace T of resistance Re against movement of the plunger rod dependent on the position P of the plunger rod. The plunger rod is moved from a retracted plunger rod position PR to an extended plunger rod position PE. In the beginning of the movement, the resistance against movement of the plunger rod is constant Ex1, e.g. the plunger rod does not yet push a stopper. Afterwards, a plunger rod front end of the plunger rod abuts a first stopper of the cartridge, and the resistance against movement of the plunger rod increases Ex2. The increased resistance is caused by the resistance against movement of the first stopper, e.g. due to frictional force. The resistance may decrease slightly after the first stopper has started moving, as illustrated. When the plunger rod approaches the extended plunger rod position PE, the resistance may increase again Ex3, e.g. due to the first stopper approaching an end of the cartridge.

The trace T is an example of resistance against plunger rod movement when the cartridge received is a new and/or unused and/or normal cartridge. Determining a cartridge parameter may be based on the resistance and/or plunger rod position. Determining the cartridge parameter may be based on one or more thresholds, such as resistance thresholds, such as a low resistance threshold Re1 and/or a high resistance threshold Re2, and/or plunger rod thresholds, such as a first plunger rod threshold P1 and/or a second plunger rod threshold P2.

Other situations, such as situations wherein the cartridge received is apparently used and/or flawed, are exemplified by additional exemplary traces, T2, T3, T4.

Trace T2 illustrates an exemplary situation wherein the resistance against movement increases above the low resistance threshold Re1 before the plunger rod position has reached the first plunger rod threshold P1. Such situation may for example indicate a flawed cartridge, or that something is blocking the plunger rod from moving. Following such situation, the plunger rod may be retracted to the retracted plunger rod position and an error message may be provided through a user interface.

Trace T3 illustrates an exemplary situation wherein the resistance against movement has not increased above the low resistance threshold Re1 before the plunger rod position has reached the second plunger rod threshold P2. Such situation may for example indicate a cartridge wherein the first stopper is in an advanced position, e.g. a used cartridge. Following such situation, the plunger rod may be retracted to the retracted plunger rod position and an error message may be provided through a user interface.

Trace T4 illustrates an exemplary situation wherein the resistance against movement increases above the high resistance threshold Re2, e.g. after the plunger rod position has passed the first plunger rod threshold P1. Such situation may for example indicate that the first stopper is blocked from moving, e.g. the cartridge may be flawed. Following such situation, the plunger rod may be retracted to the retracted plunger rod position and an error message may be provided through a user interface.

The thresholds, such as the low resistance threshold Re1, the high resistance threshold Re2, the first plunger rod threshold P1, and/or the second plunger rod threshold P2 may be individually determined for the cartridge received. For example, the processing unit of the auto injector may be configured to determine one or more of the thresholds, based on a cartridge code feature of the cartridge and/or cartridge assembly received.

Figure 10:
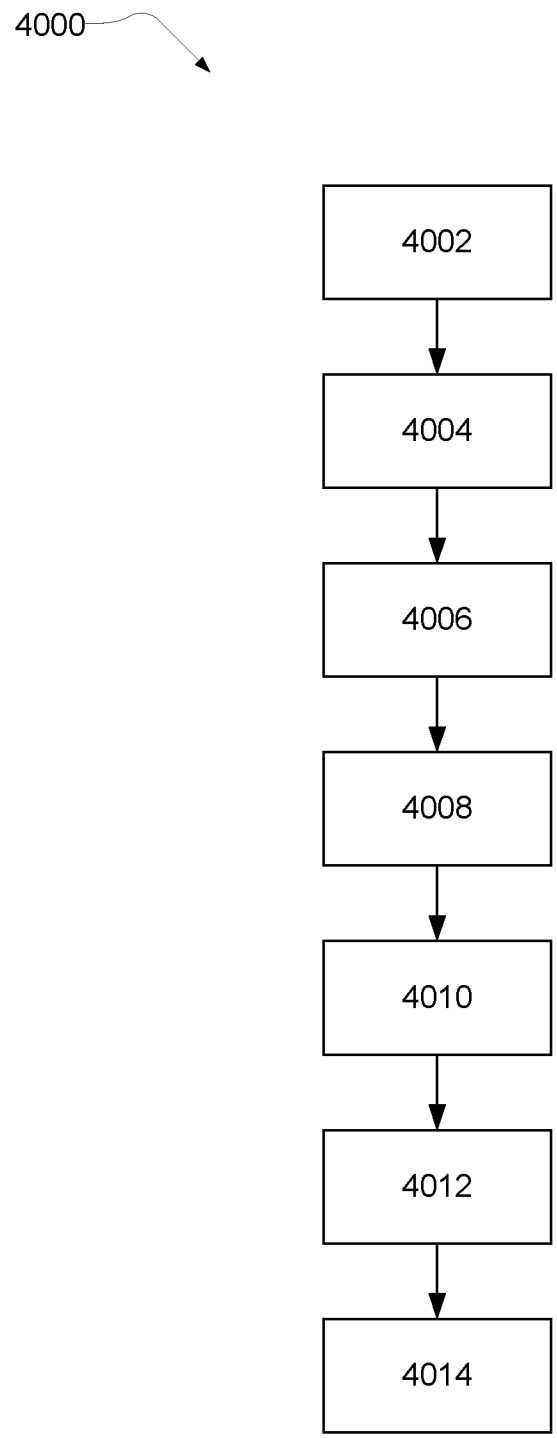
FIG. 10 shows a flow chart of an exemplary method.

FIG. 10 shows a flow chart of an exemplary method 4000 for operating an auto injector. The method 4000 comprises: receiving 4002 a first input signal; detecting 4004 reception of the cartridge, e.g. in a cartridge receiver of the auto injector; moving 4006 a plunger rod to a mix plunger rod position; determining 4008 orientation of the cartridge; moving 4010 the plunger rod to a prime plunger rod position based on the orientation of the cartridge; receiving 4012 a trigger event; and moving 4014 the plunger rod to an injection plunger rod position.

Receiving 4002 the first input signal may comprise receiving a user input signal from a user interface, e.g. originating from a user pressing a button. The first input signal may originate from a user turning on the auto injector.

Detecting 4004 reception of the cartridge may comprise detection of a user inserting the cartridge into the cartridge receiver through a cartridge receiver opening. Detecting 4004 reception of the cartridge may comprise detecting presence of a cartridge in the cartridge receiver.

Receiving 4002 the first input signal and detecting 4004 reception of the cartridge may be interchanged.

Moving 4006 the plunger rod to the mix plunger rod position may follow detection 4004 of the cartridge being received in the cartridge receiver and reception 4002 of the first input signal. For example, moving 4006 the plunger rod to the mix plunger rod position may be performed only after a cartridge is detected 4004 and the first input signal is received 4002.

Determining 4008 orientation of the cartridge may comprise determining orientation by an orientation sensor, such as an accelerometer. Determining 4008 orientation of the cartridge may comprise determining orientation of the auto injector. Determining 4008 orientation of the cartridge may comprise determining whether an outlet of the cartridge is pointing upwards.

Alternatively or additionally, moving 4006 the plunger rod to the mix plunger rod position may be preceded by determining 4008 orientation of the cartridge. For example, moving 4006 the plunger rod to the mix plunger rod position may require that the outlet of the cartridge is pointing upwards, e.g. determined by determining 4008 orientation of the cartridge.

Moving 4010 the plunger rod to a prime plunger rod position may follow completion of movement of the plunger rod to the mix plunger rod position. Moving 4010 the plunger rod to a prime plunger rod position may follow completion of movement of the plunger rod to the mix plunger rod position and an additional predetermined delay, e.g. to allow reconstitution of the medicament.

Moving 4010 the plunger rod to a prime plunger rod position may require that the outlet of the cartridge is pointing upwards, e.g. determined by determining 4008 orientation of the cartridge. Moving 4010 the plunger rod to a prime plunger rod position may be temporary paused if the orientation of the cartridge is not within a predefined range of orientations.

Receiving 4012 the trigger event may comprise receiving a user input signal from a user interface, e.g. receiving the trigger event from a trigger member, e.g. originating from a user pressing a button. The trigger event may originate from a user indicating a start of injection. The trigger event may originate from a user pressing a front part of the auto injector against an intended injection site. The trigger event may comprise a contact member signal being indicative of a contact member of the auto injector being in a first contact member position.

Moving 4014 the plunger rod to an injection plunger rod position may result in ejection of the medicament through the cartridge outlet, such as through a needle. Moving 4014 the plunger rod may follow reception of the trigger event 4012, such as after completion of movement 4010 of the plunger rod to the prime plunger rod position.

Figure 11:
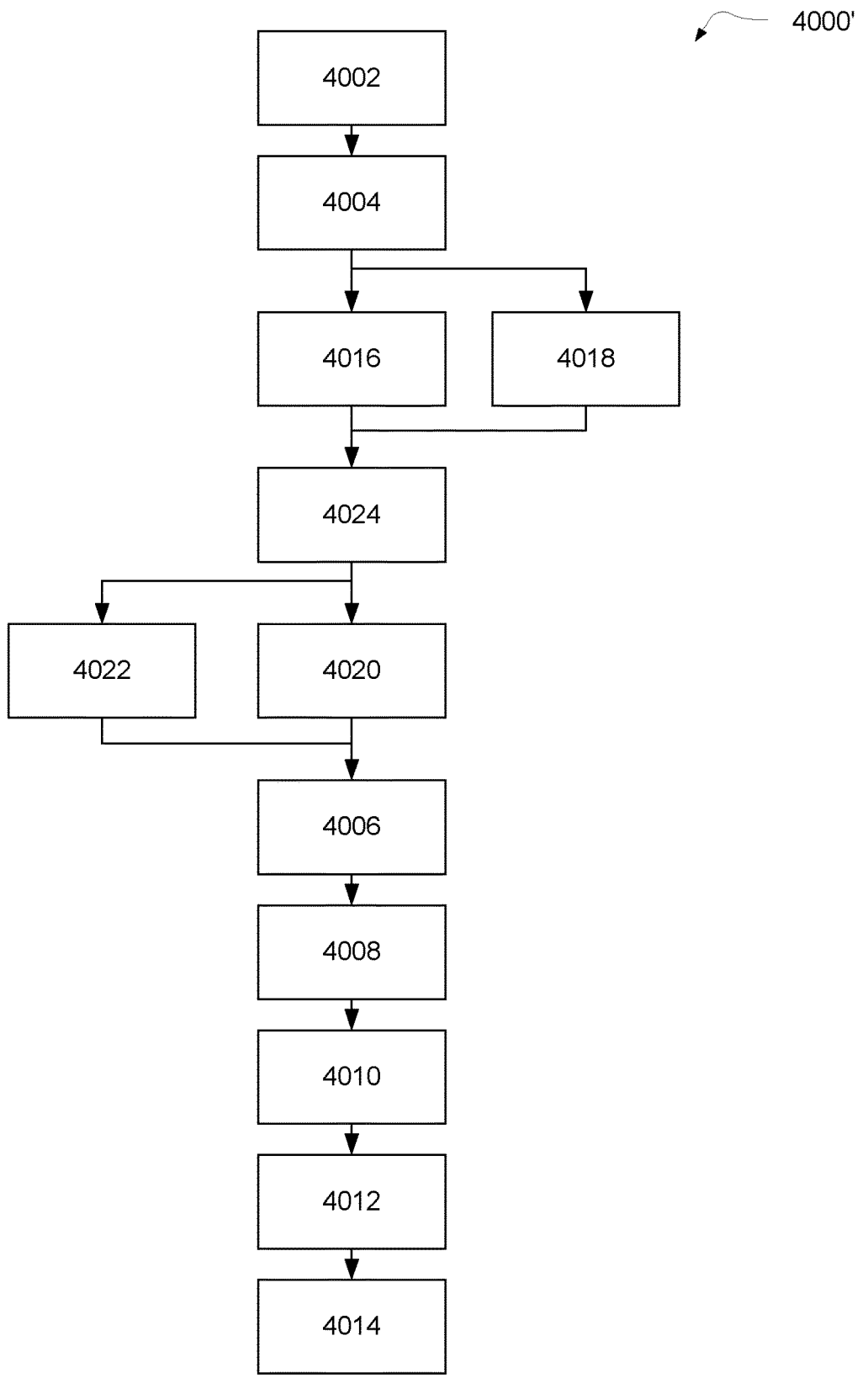
FIG. 11 shows a flow chart of an exemplary method.

FIG. 11 shows a flow chart of an exemplary method 4000'. The method 4000' comprises the same steps of the method 4000 as explained in relation to the previous figure. However the method 4000' is an example of a method comprising additional steps of reading 4016 a cartridge code feature; detecting 4018 a temperature; detecting 4024 needle cover removal; moving 4020 the plunger rod to a pre-mix plunger rod position; and detecting 4022 resistance against movement of the plunger rod.

The method 4000' comprises reading 4016 a cartridge code feature. The cartridge code feature may be indicative of one or more cartridge specifications. The subsequent steps of the method 4000' may comprise adaptations based on the cartridge specifications. For example, subsequent steps of the method 4000' may be tailored to the specific cartridge received and identified.

Detecting 4018 a temperature may comprise detecting a temperature of the cartridge and/or a temperature indicative of the temperature of the cartridge. The subsequent steps of the method 4000' may comprise adaptations based on the temperature.

Reading 4016 the cartridge code feature and detecting 4018 the temperature may be performed simultaneously, as illustrated. However, alternatively, it may be performed sequentially.

Detecting 4024 needle cover removal may be a prerequisite of initiating movement of the plunger rod. For example, needle cover removal may be indicative of intended use of the cartridge received.

Moving 4020 the plunger rod to a pre-mix plunger rod position may comprise initial movement of a first stopper of the cartridge, e.g. movement of the first stopper without commencing mixing of a two-component medicament.

Detecting 4022 resistance against movement of the plunger rod may be performed simultaneously with moving 4020 the plunger rod to the pre-mix plunger rod position, as illustrated. Detecting 4022 resistance against movement of the plunger rod may be indicative of cartridge parameters of the cartridge received, such as whether the cartridge is new or used or flawed.

Moving 4006 the plunger rod to the mix plunger rod position may follow reading 4016 the cartridge code feature, detecting 4018 the temperature, detecting 4024 needle cover removal, moving 4020 the plunger rod to the pre-mix plunger rod position, and detecting 4022 resistance against movement of the plunger rod.

Moving 4006 the plunger rod to the mix plunger rod position may be based on one or more of the cartridge code feature, the temperature, needle cover removal and/or resistance against movement of the plunger rod.

Moving 4010 the plunger rod to the prime plunger rod position may be based on one or more of the cartridge code feature, the temperature, needle cover removal and/or resistance against movement of the plunger rod.

Moving 4014 the plunger rod to the injection plunger rod position may be based on one or more of the cartridge code feature, the temperature, needle cover removal and/or resistance against movement of the plunger rod.

The method 4000 and/or the method 4000' may include a first step of receiving the cartridge.

Figure 12:
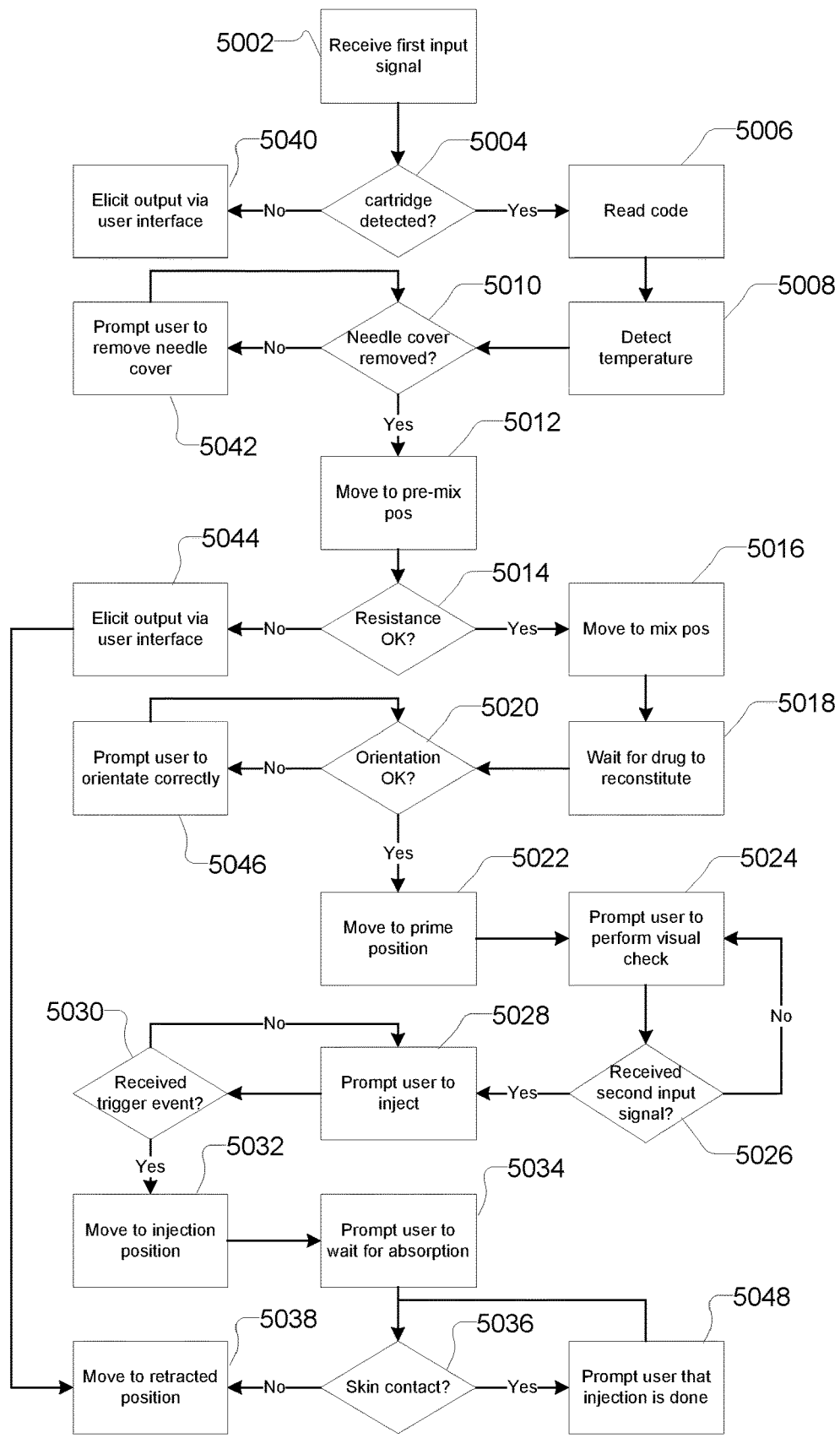
FIG. 12 shows a flow chart of an exemplary method.

FIG. 12 shows a flow chart of an exemplary implementation of the exemplary method 4000'. The flow chart shown may be an exemplary implementation in a processing unit of an auto injector.

The procedure is initiated by receiving 5002 a first input signal. A user may initiate the procedure by turning on the device thereby providing, e.g. via the user interface, the first input signal.

Following receipt 5002 of the first input signal, it is considered 5004 whether a cartridge is detected to be received in the cartridge receiver of the auto injector. If not, an output may be provided 5040 through the user interface.

If a cartridge is detected 5004, or when a cartridge is a detected 5004, after receiving 5002 the first input signal, a cartridge code feature is read 5006.

Following reading 5006 of the cartridge code feature, temperature is detected 5008, such as the temperature of the cartridge received.

Following detection 5008 of the temperature and reading 5006 of the cartridge code feature, it is detected 5010 whether a needle cover is removed, such as not present. If a needle cover is not removed, a user output may be provided, e.g. through the user interface, prompting 5042 the user to remove the needle cover. If the needle cover is removed 5010, or when the needle cover is removed 5010, the plunger rod is moved 5012 to a pre-mix plunger rod position. During this movement resistance against movement of the plunger rod is measured.

The resistance against movement is analysed 5014 to determine whether it is acceptable or not. This analysis may be based on the cartridge code feature read 5006 and/or the temperature detected 5008.

If the resistance 5014 is not acceptable, a user output may be provided 5044, e.g. via the user interface. The output may indicate that the cartridge is to be replaced. Subsequently, the plunger rod is moved 5038 to a retracted plunger rod position, such as the starting position of the plunger rod.

If the resistance 5014 is acceptable the plunger rod is moved 5016 to a mix plunger rod position, e.g. to combine a first medicament component and a second medicament component.

After the plunger rod is moved 5016 to the mix plunger rod position a delay 5018 is inserted to provide the combined medicament components to reconstitute to the medicament for injection. The delay 5018 may be between 1 and 12 min, such as between 3 and 10 min. During a delay a user output may be provided via the user interface, the user output may be indicative for the reconstitution.

After the medicament is reconstituted and/or the delay suitable for reconstitution of the medicament has lapsed 5018, the orientation of the cartridge is assessed 5020. The cartridge orientation may be assessed from measuring the orientation of the auto injector. The orientation should be acceptable for performing an air-shot, e.g. the cartridge outlet of the cartridge should be pointing upwards, such that air may be expelled and/or reduced. If the orientation 5020 is not acceptable, e.g. the cartridge outlet is not pointing upwards and/or the cartridge is not within 45 deg. of vertical, the user is prompted 5046, e.g. via the user interface, to orientate the auto injector correctly, e.g. point the cartridge outlet upwards.

If the orientation is acceptable 5020, or when the orientation is acceptable, the plunger rod is moved 5022 to a prime plunger rod position, e.g. to expel air from the cartridge compartment. The prime plunger rod position may be determined based on the cartridge code feature read 5006 and/or the temperature detected 5008.

After moving 5022 the plunger rod to the prime plunger rod position, the user is prompted, e.g. via the user interface, to perform a visual check 5024 of the medicament. For example, the user may be provided the possibility to abort the procedure if sediments of medicament are visible. To accept the visual quality of the medicament, the user may provide a second input signal, e.g. by pressing a button of the user interface. The button used for providing the second input signal may be the same button as for providing the first input signal. The prompting of the user to perform the visual check 5024 may cease and/or the procedure may be aborted if a time out, e.g. 4-5 hours, after the medicament is reconstituted and/or after the delay suitable for reconstitution of the medicament has lapsed 5018.

After receiving the second input signal 5026, the user may be prompted 5028, e.g. via the user interface, to initiate injection of the medicament. The user may inject the medicament by providing a trigger event, e.g. by pressing a contact member of the auto injector towards an intended injection site, e.g. thereby inserting the needle into the tissue of the intended injection site. While not receiving 5030 the trigger event, the user is continuously prompted to initiate injection 5028.

After receiving 5030 the trigger event, the plunger rod is moved 5032 to the injection plunger rod position, e.g. to eject the medicament of the cartridge, such as to inject the medicament into the tissue of the intended injection site.

After the plunger rod is moved 5032 to the injection plunger rod position, it may be preferred to delay retraction of the needle to allow the medicament to be distributed into the tissue. Thus, the auto injector prompts 5034 the user, e.g. via the user interface, to wait for a set dwell time, e.g. between 1 and 15 sec.

Following reception 5030 of the trigger event and/or movement 5032 of the plunger rod to the injection plunger rod position and/or prompting 5034 the user to wait for the set dwell time, skin contact is assessed 5036, e.g. whether the contact member is still pressed against the intended injection site. If, after the dwell time, the skin contact is still present, the user is prompted 5048 that injection is done and/or that the user may remove the auto injector from the injection site.

If and/or when the skin contact is lost 5036, the plunger rod is moved 5038 to the retracted plunger rod position.

After movement 5038 of the plunger rod to the retracted plunger rod position, the cartridge may be removed and discarded.

FIGS. 13A, 13B, 13C and 13D schematically illustrates an exemplary user interface 1100 of an exemplary auto injector 4, such as an auto injector 4 as illustrated in FIG. 1.

The user interface 1100 comprises a first output member 1110 as illustrated, e.g. a plurality of LEDs. The first output member 1110 may provide for a user output to a user. The first output member 1110 may be used to indicate a step in the procedure to the user and/or to indicate an error message. The first output member 1110 comprises a first LED 1116, a second LED 1118, and a third LED 1120.

The user interface 1100 may comprise a second output member (not shown), e.g. a speaker.

The user interface 1100 comprises a contact member 1102, e.g. at a forward end of the auto injector 4. The contact member 1102 may be configured to be pressed against an injection site. The contact member 1102 may serve as a third output member of the user interface 1100, e.g. the contact member 1102 may be configured to light up, such as flash.

The user interface 1100 comprises a first input member 1108, e.g. a button. The first input member 1108 may provide for a user input from a user. For example, the first input member 1108 may be used for receiving a push from a user to proceed to a next step. The first input member 1108 may serve as a fourth output member of the user interface 1100, e.g. the first input member 1108 may be configured to light up, such as flash.

Figure 13A:
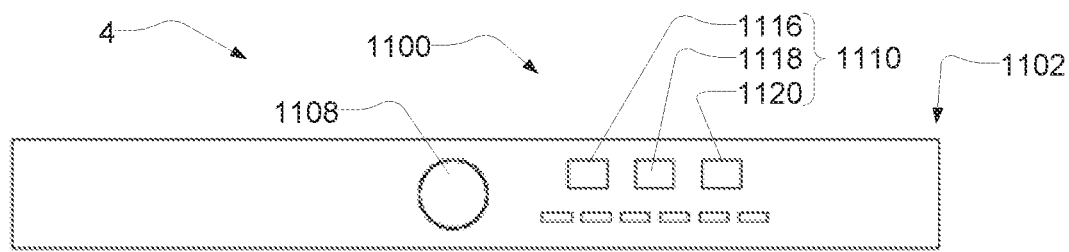
FIGS. 13A, 13B, 13C, and 13D schematically illustrate an exemplary user interface.

FIG. 13A schematically illustrates a situation of the user interface 1100 wherein none of the output members are active, e.g. the auto injector 4 may be turned off.

Figure 13B:
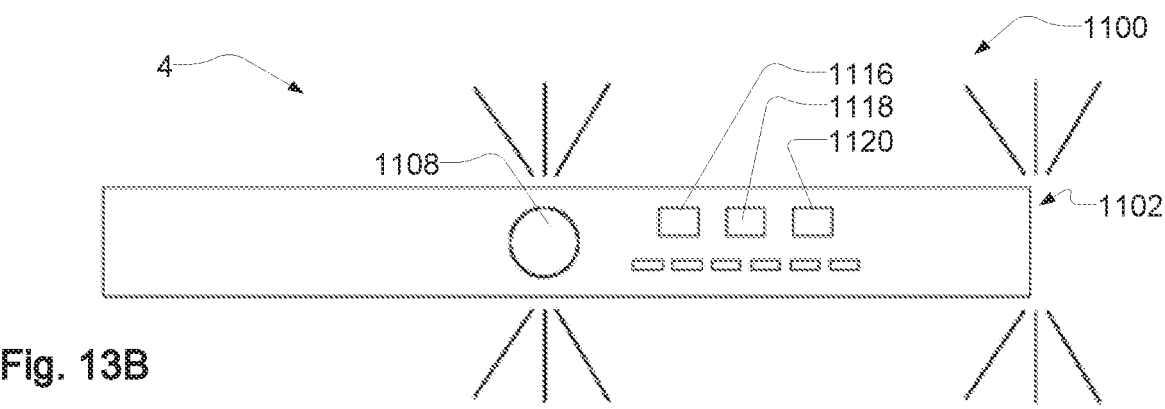

FIG. 13B schematically illustrates a situation of the user interface 1100 wherein the first input member 1108 and the contact member 1102 light up, such as flashes. The first input member 1108 and the contact member 1102 may flash synchronously and/or asynchronously. The situation shown may be a situation indicating that the user should press the first input member 1108 and/or insert a cartridge though the contact member 1102. The situation shown may be a situation following that the auto injector is turned on.

Figure 13C:
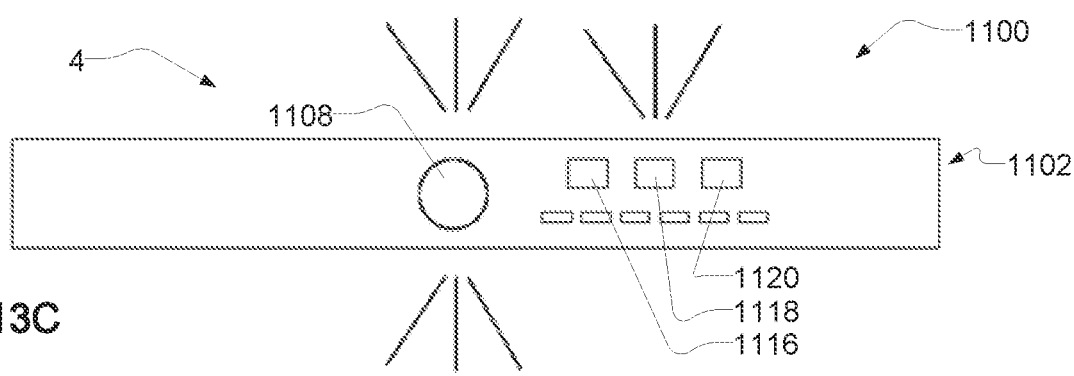

FIG. 13C schematically illustrates a situation of the user interface 1100 wherein the first input member 1108 and the second LED 1118 light up, such as flashes. The situation shown may be a situation indicating that the user should press the first input member 1108 to proceed to a next step. The situation shown may be a situation following mixing of medicament components and/or before performing an airshot.

Figure 13D:
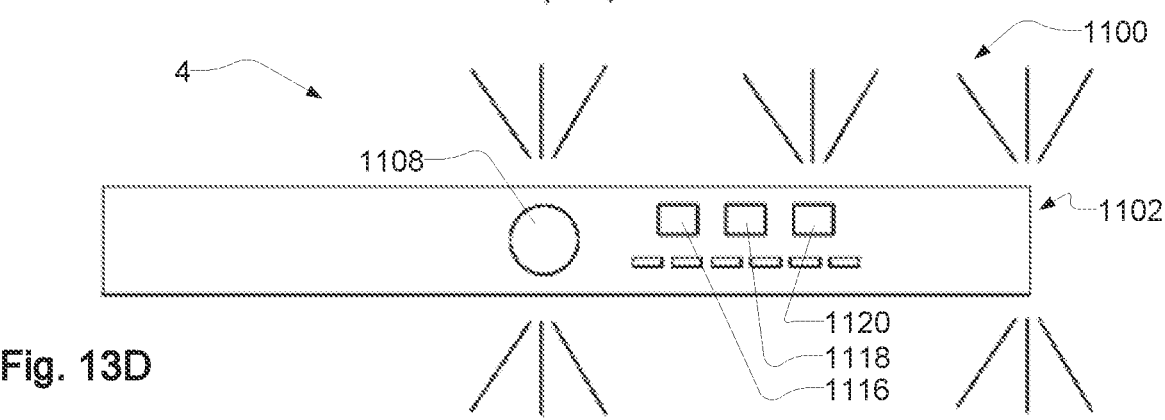

FIG. 13D schematically illustrates a situation of the user interface 1100 wherein the first input member 1108 and the contact member 1102 and the third LED 1120 light up, such as flashes. The first input member 1108 and the contact member 1102 and the third LED 1120 may flash synchronously and/or asynchronously. The situation shown may be a situation indicating that the user should press the contact member 1102 against an intended injection site to inject the medicament. The situation shown may be a situation before injecting the medicament.

Figure 14:
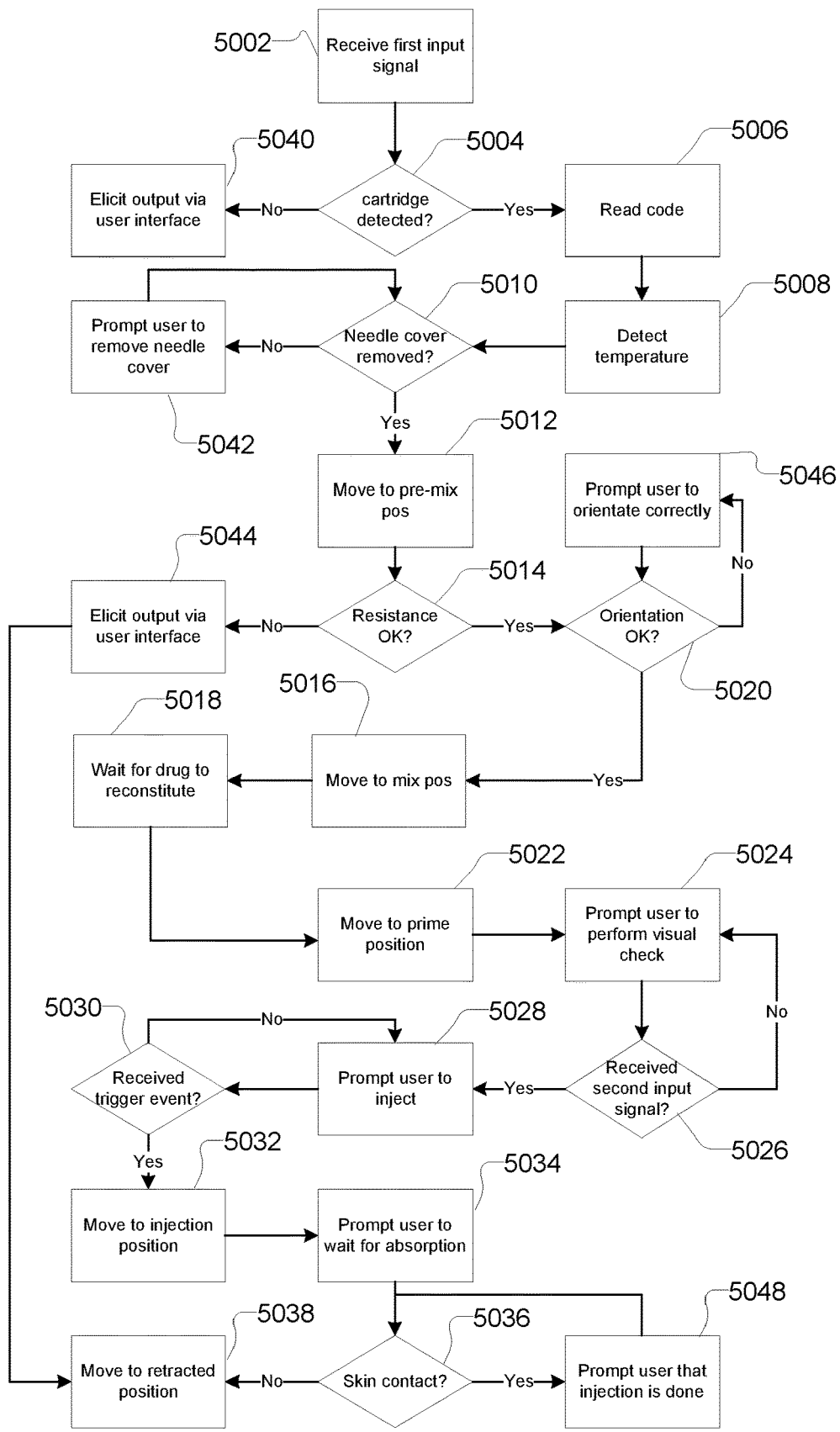
FIG. 14 shows a flow chart of an exemplary method.

FIG. 14 shows a flow chart of a variation of the exemplary implementation shown in FIG. 12. The flow chart shown may be an exemplary implementation in a processing unit of an auto injector.

The procedure is initiated by receiving 5002 a first input signal. A user may initiate the procedure by turning on the device thereby providing, e.g. via the user interface, the first input signal.

Following receipt 5002 of the first input signal, it is considered 5004 whether a cartridge is detected to be received in the cartridge receiver of the auto injector. If not, an output may be provided 5040 through the user interface.

If a cartridge is detected 5004, or when a cartridge is a detected 5004, after receiving 5002 the first input signal, a cartridge code feature is read 5006.

Following reading 5006 of the cartridge code feature, temperature is detected 5008, such as the temperature of the cartridge received.

Following detection 5008 of the temperature and reading 5006 of the cartridge code feature, it is detected 5010 whether a needle cover is removed, such as not present. If a needle cover is not removed, a user output may be provided, e.g. through the user interface, prompting 5042 the user to remove the needle cover. If the needle cover is removed 5010, or when the needle cover is removed 5010, the plunger rod is moved 5012 to a pre-mix plunger rod position. During this movement resistance against movement of the plunger rod is measured.

The resistance against movement is analysed 5014 to determine whether it is acceptable or not. This analysis may be based on the cartridge code feature read 5006 and/or the temperature detected 5008.

If the resistance 5014 is not acceptable, a user output may be provided 5044, e.g. via the user interface. The output may indicate that the cartridge is to be replaced. Subsequently, the plunger rod is moved 5038 to a retracted plunger rod position, such as the starting position of the plunger rod.

If the resistance 5014 is acceptable the orientation of the cartridge is assessed 5020. The cartridge orientation may be assessed from measuring the orientation of the auto injector. The orientation should be acceptable for combining a first medicament component and a second medicament component, e.g. to avoid excessive foaming during the process. For example, an acceptable orientation may be that the cartridge outlet of the cartridge is pointing upwards. If the orientation 5020 is not acceptable, e.g. the cartridge outlet is not pointing upwards and/or the cartridge is not within 45 deg. of vertical, the user is prompted 5046, e.g. via the user interface, to orientate the auto injector correctly, e.g. point the cartridge outlet upwards.

If the orientation is acceptable 5020, or when the orientation is acceptable, the plunger rod is moved 5016 to a mix plunger rod position, e.g. to combine the first medicament component and the second medicament component.

After the plunger rod is moved 5016 to the mix plunger rod position a delay 5018 is inserted to provide the combined medicament components to reconstitute to the medicament for injection. The delay 5018 may be between 1 and 12 min, such as between 3 and 10 min. During the delay a user output may be provided via the user interface, the user output may be indicative for the reconstitution progression. The delay may be dependent on the cartridge specification, e.g. from reading 5006 of the cartridge code feature.

After the medicament is reconstituted and/or the delay suitable for reconstitution of the medicament has lapsed 5018 the plunger rod is moved 5022 to a prime plunger rod position, e.g. to expel air from the cartridge compartment. The prime plunger rod position may be determined based on the cartridge code feature read 5006 and/or the temperature detected 5008.

Determining orientation prior to moving the plunger rod to the prime plunger rod position may be omitted, e.g. by assuming the orientation of the auto injector is maintained from when the orientation was determined prior to moving the plunger rod to the mix plunger rod position. In an alternative implementation (not shown), orientation may be determined both prior to moving the plunger rod to the mix plunger rod position and prior to moving the plunger rod to the prime plunger rod position.

After moving 5022 the plunger rod to the prime plunger rod position, the user is prompted, e.g. via the user interface, to perform a visual check 5024 of the medicament. For example, the user may be provided the possibility to abort the procedure if sediments of medicament are visible. To accept the visual quality of the medicament, the user may provide a second input signal, e.g. by pressing a button of the user interface. The button used for providing the second input signal may be the same button as for providing the first input signal. The prompting of the user to perform the visual check 5024 may cease and/or the procedure may be aborted if a time out, e.g. 4-5 hours, after the medicament is reconstituted and/or after the delay suitable for reconstitution of the medicament has lapsed 5018.

After receiving the second input signal 5026, the user may be prompted 5028, e.g. via the user interface, to initiate injection of the medicament. The user may inject the medicament by providing a trigger event, e.g. by pressing a contact member of the auto injector towards an intended injection site, e.g. thereby inserting the needle into the tissue of the intended injection site. While not receiving 5030 the trigger event, the user is continuously and/or repeatedly prompted to initiate injection 5028.

After receiving 5030 the trigger event, the plunger rod is moved 5032 to the injection plunger rod position, e.g. to eject the medicament of the cartridge, such as to inject the medicament into the tissue of the intended injection site.

After the plunger rod is moved 5032 to the injection plunger rod position, it may be preferred to delay retraction and/or removal of the needle to allow the medicament to be distributed into the tissue. Thus, the auto injector prompts 5034 the user, e.g. via the user interface, to wait for a set dwell time, e.g. between 1 and 15 sec, before he/she retracts the needle.

Following reception 5030 of the trigger event and/or movement 5032 of the plunger rod to the injection plunger rod position and/or prompting 5034 the user to wait for the set dwell time, skin contact is assessed 5036, e.g. whether the contact member is still pressed against the intended injection site. If, after the dwell time, the skin contact is still present, the user is prompted 5048 that injection is done and/or that the user may remove the auto injector from the injection site.

If and/or when the skin contact is lost 5036, the plunger rod is moved 5038 to the retracted plunger rod position.

After movement 5038 of the plunger rod to the retracted plunger rod position, the cartridge may be removed and discarded.

Exemplary auto injectors, cartridges, systems and methods are set out in the following items:

1. An auto injector for preparing and/or administering a medicament from a cartridge having a first cartridge end and a second cartridge end and having a cartridge outlet at the first cartridge end, the cartridge comprising a cartridge compartment with a first cartridge subcompartment containing a first medicament component of the medicament and a second cartridge subcompartment containing a second medicament component of the medicament, the auto injector comprising:
    a housing;
    a cartridge receiver with a cartridge receiver opening, the cartridge receiver being configured to receive the cartridge by insertion of the second end of the cartridge through the cartridge receiver opening;
    a cartridge sensor configured to detect reception of the cartridge in the cartridge receiver and provide a cartridge detection signal indicative of the cartridge being received in the cartridge receiver;
    a drive module coupled to move a plunger rod between a retracted plunger rod position and an extended plunger rod position, the plunger rod being configured to move the first stopper;
    an orientation sensor configured to provide an orientation signal indicative of the orientation of the cartridge when received in the cartridge receiver;
    a processing unit coupled to the orientation sensor, the cartridge sensor, and to the drive module;
    the processing unit being configured to:
        receive a first input signal;
        receive the cartridge detection signal;
        control the drive module to move the plunger rod to a mix plunger rod position following reception of the cartridge detection signal and the first input signal;
        receive the orientation signal; and
        control the drive module to move the plunger rod to a prime plunger rod position based on the orientation signal and following completion of movement of the plunger rod to the mix plunger rod position.

2. Auto injector according to item 1, wherein the processing unit is further configured to:
    receive a trigger event; and
    control the drive module to move the plunger rod to an injection plunger rod position following reception of the trigger event after completion of movement of the plunger rod to the prime plunger rod position.

3. Auto injector according to any of items 1 or 2, wherein the orientation sensor comprises an accelerometer.

4. Auto injector according to any of the preceding items comprising a code sensor configured to read a cartridge code feature and provide a code signal indicative of the cartridge code feature, the processing unit being coupled to the code sensor and being configured to receive the code signal.

5. Auto injector according to item 4, wherein the processing unit is configured to determine an unauthorized cartridge based on the code signal.

6. Auto injector according to any of items 4 or 5, wherein control of the drive module to move the plunger rod to the prime plunger rod position is based on the code signal.

7. Auto injector according to any of items 4-6, wherein movement of the plunger rod to the prime plunger rod position has a prime plunger rod speed, and wherein the prime plunger rod speed is based on the code signal.

8. Auto injector according to any of items 4-7, wherein movement of the plunger rod to the mix plunger rod position has a mix plunger rod speed, and wherein the mix plunger rod speed is based on the code signal.

9. Auto injector according to any of items 4-8, wherein movement of the plunger rod to the injection plunger rod position has an injection plunger rod speed, and wherein the injection plunger rod speed is based on the code signal.

10. Auto injector according to any of the preceding items comprising a resistance sensor configured to provide a resistance signal indicative of resistance against movement of the plunger rod, the processing unit being coupled to the resistance sensor and being configured to receive the resistance signal.

11. Auto injector according to item 10, wherein the processing unit is configured to determine an unauthorized cartridge based on the resistance signal.

12. Auto injector according to any of items 10 or 11, wherein the processing unit is configured to determine a cartridge parameter based on the resistance signal.

13. Auto injector according to any of items 10-12, wherein control of the drive module to move the plunger rod to the mix plunger rod position is based on the resistance signal.

14. Auto injector according to any of items 10-13, wherein the processing unit is configured to control the drive module to move the plunger rod to the mix plunger rod position only if the resistance signal indicates resistance against movement of the plunger rod above a low resistance threshold.

15. Auto injector according to any of the preceding items comprising a first input device configured to provide the first input signal, the first input signal being indicative of a first user interaction with the first input device, the processing unit being coupled to the first input device.

16. Auto injector according to any of the preceding items comprising a contact member movable between an extended contact member position and a retracted contact member position, the contact member being biased towards the extended contact member position, and the contact member being configured to be moved towards the retracted contact member position when pressed against the injection site, the contact member is configured to provide a contact member signal indicative of position of the contact member, the processing unit is coupled to the contact member and configured to receive the contact member signal.

17. Auto injector according to item 16 as dependent on item 2, the trigger event comprising the contact member signal being indicative of the contact member being in a first contact member position.

18. Auto injector according to any of items 16 or 17, wherein the contact member is configured to be in a second contact member position if a needle cover is present on the cartridge, the processing unit is configured to control the drive module to move the plunger rod to the mix plunger rod position based on the contact member signal.

19. Auto injector according to any of the preceding items, wherein the processing unit is configured to control the drive module to move the plunger rod to the prime plunger rod position only if the orientation signal indicates that a tilt angle between vertical and a longitudinal axis extending along the cartridge is within 45 degrees of vertical and the cartridge outlet is in a vertical position above the cartridge compartment.

20. Auto injector according to any of the preceding items, wherein the processing unit is configured to control the drive module to move the plunger rod to a pre-mix plunger rod position following reception of the cartridge detection signal and the first input signal, wherein movement of the plunger rod to the pre-mix plunger rod position has a pre-mix plunger rod speed, and movement of the plunger rod to the mix plunger rod position has a mix plunger rod speed, wherein the pre-mix plunger rod speed is faster than the mix plunger rod speed.

21. Auto injector according to any of the preceding items, wherein the processing unit is configured to control the drive module to move the plunger rod to the prime plunger rod position and/or to the injection plunger rod position only after a reconstitution time has elapsed since completion of the movement of the plunger rod to the mix plunger rod position.

22. Auto injector according to item 21 as dependent on any of items 4-9, wherein the reconstitution time is based on the code signal.

23. Auto injector according to any of the preceding items, wherein the processing unit is configured to control the drive module to move the plunger rod towards the retracted plunger rod position following completion of the movement of the plunger rod to the injection plunger rod position.

24. Auto injector according to any of the preceding items, wherein the processing unit is configured to control the drive module to move the plunger rod towards the retracted position only after a dwell time has elapsed since completion of the movement of the plunger rod to the injection plunger rod position.

25. Auto injector according to any of the preceding items, wherein the processing unit is configured to provide a user output via a user interface after a dwell time has elapsed since completion of the movement of the plunger rod to the injection plunger rod position.

26. Auto injector according to any of the preceding items, wherein control of the drive module to move the plunger rod to the mix plunger rod position is based on the orientation signal.

27. Auto injector according to item 26, wherein the processing unit is configured to control the drive module to move the plunger rod to the mix plunger rod position only if the orientation signal indicates that a tilt angle between vertical and a longitudinal axis extending along the cartridge is within 45 degrees of vertical and the cartridge outlet is in a vertical position above the cartridge compartment.

28. Auto injector according to any of the preceding items, wherein movement of the plunger rod to the mix plunger rod position locks the cartridge in the cartridge receiver.

29. Auto injector according to any of the preceding items, wherein movement of the plunger rod to the retracted plunger rod position unlocks the cartridge in the cartridge receiver.

30. Auto injector according to any of the preceding items, wherein the medicament is human growth hormone, such as a medicament with the formulation code ACP-011.

31. A cartridge for an auto injector comprising a first cartridge end and a second cartridge end and having a cartridge outlet at the first cartridge end, the cartridge comprising a cartridge compartment with a first cartridge subcompartment containing a first medicament component of the medicament and a second cartridge subcompartment containing a second medicament component of the medicament, the cartridge being configured to be received by a cartridge receiver of an auto injector according to any of the preceding items by insertion of the second cartridge end of the cartridge through the cartridge receiver opening of the auto injector.

32. A system comprising an auto injector according to any of items 1-30, and a cartridge according to item 31.

33. A method for operating an auto injector comprising a plunger rod and a cartridge receiver configured to receive a cartridge, the cartridge having a first cartridge end and a second cartridge end and having a cartridge outlet at the first cartridge end, the cartridge comprising a cartridge compartment with a first cartridge subcompartment containing a first medicament component of the medicament and a second cartridge subcompartment containing a second medicament component of the medicament, the method comprising:
  receiving a first input signal;
  detecting reception of the cartridge in the cartridge receiver;
  moving the plunger rod to a mix plunger rod position following detection of the cartridge being received in the cartridge receiver and reception of the first input signal;
  determining orientation of the cartridge; and
  moving the plunger rod to a prime plunger rod position based on the orientation of the cartridge and following completion of movement of the plunger rod to the mix plunger rod position.

34. Method according to item 33 further comprising:
  receiving a trigger event; and
  moving the plunger rod to an injection plunger rod position following reception of the trigger event after completion of movement of the plunger rod to the prime plunger rod position.

The invention claimed is:

1. An auto injector for preparing or administering a medicament from a cartridge having a first cartridge end and a second cartridge end and having a cartridge outlet at the first cartridge end, the cartridge comprising a cartridge compartment with a first cartridge subcompartment containing a first medicament component of the medicament and a second cartridge subcompartment containing a second medicament component of the medicament, the auto injector comprising:
  a housing;
  a cartridge receiver with a cartridge receiver opening, the cartridge receiver being configured to receive the cartridge by insertion of the second end of the cartridge through the cartridge receiver opening;
  a code sensor configured to detect reception of the cartridge in the cartridge receiver and provide a cartridge detection signal indicative of the cartridge being received in the cartridge receiver, read a cartridge code feature and provide a code signal indicative of the cartridge code feature;
  a drive module coupled to move a plunger rod between a retracted plunger rod position and an extended plunger rod position, the plunger rod being configured to move a first stopper;
  an orientation sensor configured to provide an orientation signal indicative of the orientation of the cartridge when received in the cartridge receiver; and
  a processing unit coupled to the orientation sensor, the code sensor, and to the drive module;
  the processing unit being configured to:
    receive a first input signal;
    receive the cartridge detection signal;
    receive the code signal;
    receive the orientation signal;
    control the drive module to move the plunger rod to a mix plunger rod position following reception of the cartridge detection signal and the first input signal; and
    control the drive module to move the plunger rod to a prime plunger rod position following completion of movement of the plunger rod to the mix plunger rod position, wherein movement of the plunger rod to the mix plunger rod position and/or the prime plunger rod position and/or an injection plunger rod position is based on the code signal.

2. The auto injector according to claim 1, wherein the processing unit is further configured to:
  receive a trigger event; and
  control the drive module to move the plunger rod to an injection plunger rod position following reception of the trigger event after completion of movement of the plunger rod to the prime plunger rod position.

3. The auto injector according to claim 1, wherein the orientation sensor comprises an accelerometer.

4. The auto injector according to claim 1, wherein the processing unit is configured to determine an unauthorized cartridge based on the code signal.

5. The auto injector according to claim 1, wherein movement of the plunger rod to the prime plunger rod position has a prime plunger rod speed, and wherein the prime plunger rod speed is based on the code signal.

6. The auto injector according to claim 1, wherein movement of the plunger rod to the mix plunger rod position has a mix plunger rod speed, and wherein the mix plunger rod speed is based on the code signal.

7. The auto injector according to claim 1, wherein movement of the plunger rod to the injection plunger rod position has an injection plunger rod speed, and wherein the injection plunger rod speed is based on the code signal.

8. The auto injector according to claim 1, comprising a resistance sensor configured to provide a resistance signal indicative of resistance against movement of the plunger rod, the processing unit being coupled to the resistance sensor and being configured to receive the resistance signal.

9. The auto injector according to claim 8, wherein the processing unit is configured to determine an unauthorized cartridge based on the resistance signal.

10. The auto injector according to claim 8, wherein the processing unit is configured to determine a cartridge parameter based on the resistance signal.

11. The auto injector according to claim 8, wherein control of the drive module to move the plunger rod to the mix plunger rod position is based on the resistance signal.

12. The auto injector according to claim 8, wherein the processing unit is configured to control the drive module to move the plunger rod to the mix plunger rod position only if the resistance signal indicates resistance against movement of the plunger rod above a low resistance threshold.

13. The auto injector according to claim 1, comprising a first input device configured to provide the first input signal, the first input signal being indicative of a first user interaction with the first input device, the processing unit being coupled to the first input device.

14. The auto injector according to claim 1, comprising a contact member movable between an extended contact member position and a retracted contact member position, the contact member being biased towards the extended contact member position, and the contact member being configured to be moved towards the retracted contact member position when pressed against the injection site, the contact member also being configured to provide a contact member signal indicative of position of the contact member, and wherein the processing unit is coupled to the contact member and is configured to receive the contact member signal.

15. The auto injector according to claim 14,
  wherein the processing unit is further configured to:
    receive a trigger event; and control the drive module to move the plunger rod to an injection plunger rod position following reception of the trigger event after completion of movement of the plunger rod to the prime plunger rod position, wherein the trigger event comprises the contact member signal being indicative of the contact member being in a first contact member position.

16. The auto injector according to claim 14, wherein the contact member is configured to be in a second contact member position if a needle cover is present on the cartridge, and the processing unit is configured to control the drive module to move the plunger rod to the mix plunger rod position based on the contact member signal.

17. The auto injector according to claim 1, wherein control of the drive module to move the plunger rod to the prime plunger rod position is based on the orientation signal.

18. The auto injector according to claim 17, wherein the processing unit is configured to control the drive module to move the plunger rod to the prime plunger rod position only if the orientation signal indicates that a tilt angle between vertical and a longitudinal axis extending along the cartridge is within 45 degrees of vertical and the cartridge outlet is in a vertical position above the cartridge compartment.

19. The auto injector according to claim 1, wherein the processing unit is configured to control the drive module to move the plunger rod to a pre-mix plunger rod position following reception of the cartridge detection signal and the first input signal, wherein movement of the plunger rod to the pre-mix plunger rod position has a pre-mix plunger rod speed, and movement of the plunger rod to the mix plunger rod position has a mix plunger rod speed, wherein the pre-mix plunger rod speed is faster than the mix plunger rod speed.

20. The auto injector according to claim 1, wherein the processing unit is configured to control the drive module to move the plunger rod to the prime plunger rod position or to the injection plunger rod position only after a reconstitution time has elapsed since completion of the movement of the plunger rod to the mix plunger rod position.

21. The auto injector according to claim 20, wherein the reconstitution time is based on the code signal.

22. The auto injector according to claim 1, wherein the processing unit is configured to control the drive module to move the plunger rod towards the retracted plunger rod position following completion of the movement of the plunger rod to the injection plunger rod position.

23. The auto injector according to claim 1, wherein the processing unit is configured to control the drive module to move the plunger rod towards the retracted position only after a dwell time has elapsed since completion of the movement of the plunger rod to the injection plunger rod position.

24. The auto injector according to claim 1, wherein the processing unit is configured to provide a user output via a user interface after a dwell time has elapsed since completion of the movement of the plunger rod to the injection plunger rod position.

25. The auto injector according to claim 1, wherein control of the drive module to move the plunger rod to the mix plunger rod position is based on the orientation signal.

26. The auto injector according to claim 25, wherein the processing unit is configured to control the drive module to move the plunger rod to the mix plunger rod position only if the orientation signal indicates that a tilt angle between vertical and a longitudinal axis extending along the cartridge is within 45 degrees of vertical and the cartridge outlet is in a vertical position above the cartridge compartment.

27. The auto injector according to claim 1, wherein movement of the plunger rod to the mix plunger rod position locks the cartridge in the cartridge receiver.

28. The auto injector according to claim 1, wherein movement of the plunger rod to the retracted plunger rod position unlocks the cartridge in the cartridge receiver.

29. The auto injector according to claim 1, wherein the medicament is a human growth hormone.

30. A cartridge for an auto injector comprising a first cartridge end and a second cartridge end and having a cartridge outlet at the first cartridge end, the cartridge comprising a cartridge compartment with a first cartridge subcompartment containing a first medicament component of the medicament and a second cartridge subcompartment containing a second medicament component of the medicament, the cartridge being configured to be received by a cartridge receiver of an auto injector according to claim 1 by insertion of the second cartridge end of the cartridge through the cartridge receiver opening of the auto injector.

31. A system comprising an auto injector according to claim 1, and a cartridge, the cartridge comprising a first cartridge end and a second cartridge end and having a cartridge outlet at the first cartridge end, the cartridge comprising a cartridge compartment with a first cartridge subcompartment containing a first medicament component of the medicament and a second cartridge subcompartment containing a second medicament component of the medicament, the cartridge being configured to be received by the cartridge receiver of the auto injector.

32. A method for operating an auto injector comprising a plunger rod and a cartridge receiver configured to receive a cartridge, the cartridge having a first cartridge end and a second cartridge end and having a cartridge outlet at the first cartridge end, the cartridge comprising a cartridge compartment with a first cartridge subcompartment containing a first medicament component of the medicament and a second cartridge subcompartment containing a second medicament component of the medicament, the method comprising:
receiving a first input signal;
detecting reception of the cartridge in the cartridge receiver;
reading the cartridge code feature;
determining orientation of the cartridge;
moving the plunger rod to a mix plunger rod position following detection of the cartridge being received in the cartridge receiver and reception of the first input signal; and
moving the plunger rod to a prime plunger rod position following completion of movement of the plunger rod to the mix plunger rod position, wherein movement of the plunger rod to the mix plunger rod position and/or the prime plunger rod position is based on the code signal.

33. The method according to claim 32, further comprising:
receiving a trigger event; and
moving the plunger rod to an injection plunger rod position following reception of the trigger event after completion of movement of the plunger rod to the prime plunger rod position.

34. The method according to claim 32, wherein moving the plunger rod to the mix plunger rod position is based on the orientation of the cartridge.

35. The method according to claim 32, wherein moving the plunger rod to the prime plunger rod position is based on the orientation of the cartridge.

* * * * *